(12) United States Patent
Shih et al.

(10) Patent No.: US 7,645,453 B2
(45) Date of Patent: Jan. 12, 2010

(54) ALPHA-ENOLASE SPECIFIC ANTIBODY AND METHOD OF USE

(75) Inventors: Neng-Yao Shih, Taipei (TW); Gee-Chen Chang, Taichung (TW); Ko-Jiunn Liu, Taichung (TW)

(73) Assignee: National Health Research Institutes, Miaolo County (TW)

( * ) Notice: Subject to any disclaimer, the term of this patent is extended or adjusted under 35 U.S.C. 154(b) by 0 days.

(21) Appl. No.: 11/648,132

(22) Filed: Dec. 29, 2006

(65) Prior Publication Data

US 2007/0172487 A1 Jul. 26, 2007

Related U.S. Application Data

(60) Provisional application No. 60/755,218, filed on Dec. 30, 2005.

(51) Int. Cl.
*A61K 39/00* (2006.01)
(52) U.S. Cl. .................................. 424/184.1; 435/7.23
(58) Field of Classification Search ....................... None
See application file for complete search history.

(56) References Cited

U.S. PATENT DOCUMENTS

| | | | |
|---|---|---|---|
| 5,521,285 A | 5/1996 | Pomato et al. | |
| 2007/0077583 A1* | 4/2007 | Georges et al. ................ | 435/6 |

OTHER PUBLICATIONS

Dranoff, G, Oct. 2002, vol. 188, pp. 147-154.*
Abbas, A.K. et al., "Cellular and Molecular Immunology," W.B. Saunders Company, 386-391(2000).
Altenberg, B. et al., "Genes of glycolysis are ubiquitously overexpressed in 24 cancer classes," Genomics, 84:1014-1020 (2004).
Amirghofran, Z. et al., "Soluble HLA class I molecules in malignant pleural and peritoneal effusions and its possible role on NK and LAK cytotoxicity," J Cancer Res Clin Oncol, 128:443-448. Epub 2002 Aug. 2009.
Andrews, B.S., "The role of immune complexes in the pathogenesis of pleural effusions," Am Rev Respir Dis, 124:115-120 (1981).
Barnes, D.M. et al., "Immunohistochemical determination of oestrogen receptor: comparison of different methods of assessment of staining and correlation with clinical outcome of breast cancer patients," Br J Cancer, 74:1445-1451 (1996).
Chang, G.C., et al., "Identification of α-Enolase as an Autoantigen in Lung Cancer: Its Overexpression Is Associated with Clinical Outcomes," Clin. Cancer Res. 12(19): 5746-5754 (2006).
Chang, Y.S. et al., "Enolase-α is frequently down-regulated in non-small cell lung cancer and predicts aggressive biological behavior," Clin Cancer Res, 9:3641-3644 (2003).
Chen, Y.M. et al., "Double signal stimulation was required for full recovery of the autologous tumor-killing effect of effusion-associated lymphocytes," Chest, 122:1421-1427 (2002).
Chen, Y.T., "Cancer vaccine: identification of human tumor antigens by SEREX," Cancer J, 6:S208-217 (2000).

Chu, Y.W. et al., "Selection of invasive and metastatic subpopulations from a human lung adenocarcinoma cell line," Am J Respir Cell Mol Biol, 17:353-36 (1997).
Collins, F.S. et al., "Cancer Genetics." In E. Braunwald et al., eds. *Harrison's Principles of Internal Medicine*, 15th ed. (NY: McGraw-Hill, 2001), pp. 503-509.
Dong, H., "Costimulating aberrant T cell responses by B7-H1 autoantibodies in rheumatoid arthritis," J Clin Invest, 111:363-370 (2003).
Dong, H. et al., "Tumor-associated B7-H1 promotes T-cell apoptosis: a potential mechanism of immune evasion," Nat Med, 8:793-800. Epub 2002 Jun. 2024.
Fenton, R.G. et al., "Cell Biology of Cancer." In E. Braunwald et al., eds. *Harrison's Principles of Internal Medicine*, 15th ed. (NY: McGraw-Hill, 2001), pp. 509-517.
Gatenby, R.A. et al., "Why do cancers have high aerobic glycolysis?," Nat Rev Cance,r 4:891-899 (2004).
Gharahdaghi, F. et al., "Mass spectrometric identification of proteins from silver-stained polyacrylamide gel: a method for the removal of silver ions to enhance sensitivity," Electrophoresis, 20:601-605 (1999).
Ghosh, A.K. et al., "MBP-1 physically associates with histone deacetylase for transcriptional repression," Biochem Biophys Res Commun, 260:405-409 (1999).
Giallongo, A. et al., "Molecular cloning and nucleotide sequence of a full-length cDNA for human alpha-enolase," Proc Natl Acad Sci U S A, 83:6741-6745 (1986).
Gitlits, V.M. et al., "Disease association, origin, and clinical relevance of autoantibodies to the glycolytic enzyme enolase," J Investig Med, 49:138-145 (2001).
Gomm, S.A. et al., "The value of tumour markers in lung cancer," Br J Cancer, 58:797-804 (1988).
Gorsky, Y. et al., "Complexes of breast-cancer-associated antigen (s) and corresponding antibodies in pleural effusions from a patients [sic] with breast cancer," Isr J Med Sci, 13:844-847 (1977).
Hennipman, A. et al., "Glycolytic enzymes in breast cancer, benign breast disease and normal breast tissue," Tumor Biol, 251-263 (1987).
Holland, J.P. et al., "Homologous nucleotide sequences at the 5' termini of messenger RNAs synthesized from the yeast enolase and glyceraldehyde-3-phosphate dehydrogenase gene families. The primary structure of a third yeast glyceraldehyde-3-phosphate dehydrogenase gene," J Biol Chem, 258:5291-5299 (1983).
Jiang, B.H. et al., "V-SRC induces expression of hypoxia-inducible factor 1 (HIF-1) and transcription of genes encoding vascular endothelial growth factor and enolase 1: involvement of HIF-1 in tumor progression," Cancer Res, 57:5328-5335 (1997).

(Continued)

*Primary Examiner*—Misook Yu
(74) *Attorney, Agent, or Firm*—Finnegan, Henderson, Farabow, Garrett & Dunner LLP

(57) ABSTRACT

This invention relates to a method of monitoring cancer development by determining the abundance of alpha-enolase protein wherein increased abundance is an indication of the severity of cancer. In another embodiment, the invention relates to a method of detecting cancer malignancy by determining the abundance of alpha-enolase antibodies in a sample wherein low levels of such antibodies indicates the malignancy of cancer. Also provided is a method of suppressing tumor growth by inducing the anti-ENO1 immune response.

5 Claims, 22 Drawing Sheets

OTHER PUBLICATIONS

Kim, J.W. et al., "Multifaceted roles of glycolytic enzymes," Trends Biochem Sci, 30:142-150 (2005).

Kim, J.W. et al., "Evaluation of myc E-box phylogenetic footprints in glycolytic genes by chromatin immunoprecipitation assays," Mol Cell Biol, 24:5923-5936 (2004).

Lai, C.L. et al., "Presence of serum anti-p53 antibodies is associated with pleural effusion and poor prognosis in lung cancer patients," Clin Cancer Res, 4:3025-3030 (1998).

Light, R.W., "Disorders of the Pleura, Mediastinum, and Diaphragm." In E. Braunwald et al., eds. *Harrison's Principles of Internal Medicine*, 15th ed. (NY: McGraw-Hill, 2001), p. 1513-1516.

Liu et al., "Chimeric Mouse-Human IgG1 Antibody that Can Mediate Lysis of Cancer Cells," Proc Natl Acad Sci U S A., 84(10):3439-43 (1987).

Masuda, N. et al., "Establishment and characterization of 20 human non-small cell lung cancer cell lines in a serum-free defined medium (ACL-4)," Chest, 100:429-438 (1991).

Miedouge, M. et al., "Evaluation of seven tumour markers in pleural fluid for the diagnosis of malignant effusions," Br J Cancer, 81:1059-1065 (1999).

Miyazaki, A. et al., "Cytotoxicity of histocompatibility leukocyte antigen-DR8-restricted CD4 killer T cells against human autologous squamous cell carcinoma," Jpn J Cancer Res, 88:191-197 (1997).

Muller, A.J. et al., "Inhibition of indoleamine 2,3-dioxygenase, an immunoregulatory target of the cancer suppression gene Bin1, potentiates cancer chemotherapy," Nat Med, 11:312-319. Epub 2005 Feb. 2013.

Nakashima, M. et al., "Inhibition of cell growth and induction of apoptotic cell death by the human tumor-associated antigen RCAS1," Nat Med, 5:938-942 (1999).

Nesterenko, M.V. et al., "A simple modification of Blum's silver stain method allows for 30 minute detection of proteins in polyacrylamide gels," J Biochem Biophys Methods, 28:239-242 (1994).

Pancholi, V., "Multifunctional alpha-enolase: its role in diseases," Cell Mol Life Sci, 58:902-920 (2001).

Peebles, K.A. et al., "Proteomic analysis of a neoplastic mouse lung epithelial cell line whose tumorigenicity has been abrogated by transfection with the gap junction structural gene for connexin 43, Gja1," Carcinogenesis, 24:651-657 (2003).

Perkins, D.N. et al., "Probability-based protein identification by searching sequence databases using mass spectrometry data," Electrophoresis, 20:3551-3567 (1999).

Ray, R. et al., Cloning and characterization of a human c-myc promoter-binding protein. Mol Cell Biol, 11:2154-2161 (1991).

Ray, R.B. et al., "Separate domains of MBP-1 involved in c-myc promoter binding and growth suppressive activity," Gene 186:175-180 (1997).

Ray, R.B. et al., "Human breast carcinoma cells transfected with the gene encoding a c-myc promoter-binding protein (MBP-1) inhibits tumors in nude mice," Cancer Res, 55:3747-3751 (1995).

Redlitz, A. et al., "The role of an enolase-related molecule in plasminogen binding to cells," Eur J Biochem, 227:407-415 (1995).

Rhodes, A. et al., "Reliability of immunohistochemical demonstration of oestrogen receptors in routine practice: interlaboratory variance in the sensitivity of detection andevaluation of scoring systems," J Clin Pathol, 53:125-130 (2000).

Sato, N. et al., "Human CD8 and CD4 T cell epitopes of epithelial cancer antigens," Cancer Chemother Pharmacol, 46:S86-90 (2000).

Schrama et al., "Antibody targeted drugs as cancer therapeutics," Nat Rev Drug Discov. 5(2):147-59 (2006).

Semenza, G.L. et al., "Hypoxia response elements in the aldolase A, enolase 1, and lactate dehydrogenase A gene promoters contain essential binding sites for hypoxia-inducible factor 1," J Biol Chem, 271:32529-32537 (1996).

Shih, N.Y. et al., "Congenital nephrotic syndrome in mice lacking CD2-associated protein," Science, 286:312-315 (1999).

Ueyama, H., et al., "Specific protein interacting with a tumor promoter, debromoaplysiatoxin, in bovine serum is alpha 1-acid glycoprotein," J Cancer Res Clin Oncol, 121:211-218 (1995).

Wang, D.Y., et al., "Serial antinuclear antibodies titer in pleural and pericardial fluid," Eur Respir J 15:1106-1110 (2000).

Wu, W., et al., "Identification and validation of metastasis-associated proteins in head and neck cancer cell lines by two-dimensional electrophoresis and mass spectrometry," Clin Exp Metastasis, 19:319-326 (2002).

Yamamoto, A., et al., "L-Myc overexpression and detection of autoantibodies against L-Myc in both the serum and pleural effusion from a patient with non-small cell lung cancer," Intern Med, 36:724-727 (1997).

Zeng, C.Q., et al., "Characterization of a lung cancer-associated auto-antigen," Int J Cancer, 52:523-529 (1992).

Zhang, L., et al., "Suppression subtractive hybridization to identify gene expressions in variant and classic small cell lung cancer cell lines," J Surg Res, 93:108-119 (2000).

\* cited by examiner

| Observed | Mr(expt) | Mr(calc) | Delta | Start | End | Peptide | |
|---|---|---|---|---|---|---|---|
| 640.80 | 1279.59 | 1279.58 | 0.01 | 93 - | 103 | LMLEMDGTENK | SEQ ID NO. 11 |
| 703.90 | 1405.79 | 1405.71 | 0.08 | 16 - | 28 | GNPTVEVDLFTSK | SEQ ID NO. 12 |
| 713.40 | 1424.79 | 1424.72 | 0.07 | 270 - | 281 | YISPDQLADLYK | SEQ ID NO. 13 |
| 817.40 | 1632.79 | 1632.81 | -0.03 | 344 - | 358 | VNQIGSVTESLQACK | SEQ ID NO. 14 |
| 981.00 | 1959.99 | 1959.92 | 0.07 | 203 - | 221 | DATNVGDEGGFAPNILENK | SEQ ID NO. 15 |
| 1017.00 | 2031.99 | 2032.05 | -0.06 | 307 - | 326 | FTASAGIQVVGDDLTVTNPK | SEQ ID NO. 16 |

A.

B.

A. Migration

B. Invasion

ALPHA-ENOLASE SPECIFIC ANTIBODY AND METHOD OF USE

DESCRIPTION OF THE INVENTION

This application claims the benefit of U.S. Provisional Application No. 60/755,218, filed Dec. 30, 2005, which is incorporated herein by reference.

FIELD OF THE INVENTION

The present invention relates to a method of monitoring cancer development by determining the abundance of alpha-enolase proteins (ENO1) in cancer cells. The present invention also relates to a method of detecting cancer and malignant cancer by determining the abundance of anti-ENO1 antibodies in serum and pleural effusions. Also described is a method of suppressing tumor growth by inducing an anti-ENO1 immune response.

BACKGROUND OF THE INVENTION

Tumors result from aberrant, unrestrained proliferation of a single cell, generating a clone of transformed cells (47). Cancer is characterized by tumor cells' autonomous growth and metastasis to distant sites (48).

Tumor cells may express unique antigens that can be recognized by the immune system. Tumor-associated antigens include, but are not limited to, mutated oncogenes, mutated normal cellular proteins, aberrantly expressed cellular proteins, abnormal cell-surface proteins, and oncogenic viral proteins (49). Ideally, the immune system views these tumor-associated antigens as non-self, eradicating the tumor cells while sparing the healthy cells. Thus, identification of immunogenic tumor-associated antigens promotes clinical prognostic or therapeutic applications for cancer.

Such malignancies may be indicated in pleural effusion, excess fluid in the space between the lung and chest wall (50). Lung carcinoma, breast carcinoma, and lymphoma cause about 75% of all malignant pleural effusions (50). Malignant pleural effusion may be enriched with lymphocytic infiltrates and tumor cells. Tumor-associated immune complexes (1-3) or autoantibodies such as anti-p53 (4), antinuclear (5), and anti-L-Myc (6) antibodies have been found in effusion fluids and are associated with poor prognosis. Several lung tumor-associated antigens have also been identified in malignant effusion, including, cytokeratin 19 fragments, neuron-specific enolase (ENO2), squamous cell carcinoma antigen (7), and soluble HLA-I (8) etc.

SUMMARY OF THE INVENTION

The invention relates to a method of monitoring cancer development, comprising determining the abundance of alpha-enolase proteins (ENO1) in cancer cells, wherein increased abundance correlates with cancer severity. In one embodiment, the abundance is determined by measuring the binding of an ENO1 specific antibody to the ENO1 proteins.

Further provided is a method of producing the ENO1 specific antibody, comprising using primers comprising SEQ ID NO: 1 and SEQ ID NO: 2 or degenerate variants thereof to obtain ENO1 cDNA for cloning, expressing the cloned gene to obtain a recombinant protein, and using the recombinant protein to produce polyclonal or monoclonal antibody.

Also provided is a method of detecting cancer comprising determining the abundance of ENO1-specific antibodies in serum samples, wherein a low level of ENO1-specific antibodies indicates the presence of a malignant tumor.

Furthermore, the invention provides a method of suppressing tumor growth comprising inducing an anti-ENO1 immune response.

Additional aspects of the invention will be set forth in part in the description which follows, and in part will be obvious from the description, or may be learned by practice of the invention.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

Figure 5A:
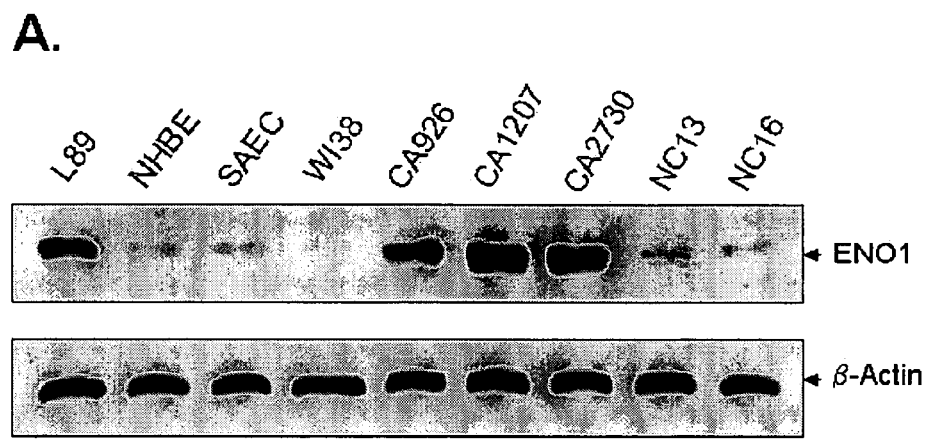

FIG. 5A shows Western blots of effusion tumor cells. L89, CA926, CA1207, and CA2730 are lung effusion tumor cells. NC13 and NC16 are effusion cells from patients with non-cancer-associated diseases. Normal human lung primary epithelial cells, normal human bronchial epithelial cells (NHBE) and small airway epithelial cells (SAEC), and a lung embryonic fibroblast cell line (WI38) served as controls. Blots were probed with ENO1 antiserum, as described in Example 6. After stripping, the same blot was re-probed with antibodies specific to β-actin as a loading control. These data show overexpression of ENO1 in effusion tumor cells.

Figure 5B:
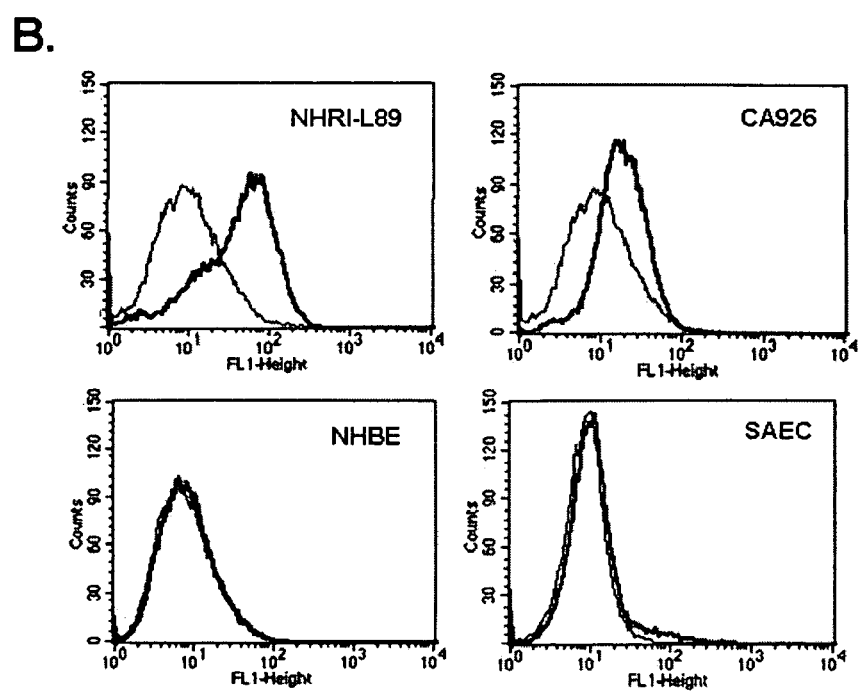

FIG. 5B shows flow cytometric analysis of intact L89 cells, CA926 cells, and control lung cells, after cell-surface staining with ENO1 antiserum, according to Example 6. These data show increased cell surface-localized ENO1 expression on cancer cells compared to control cells.

Figure 6:
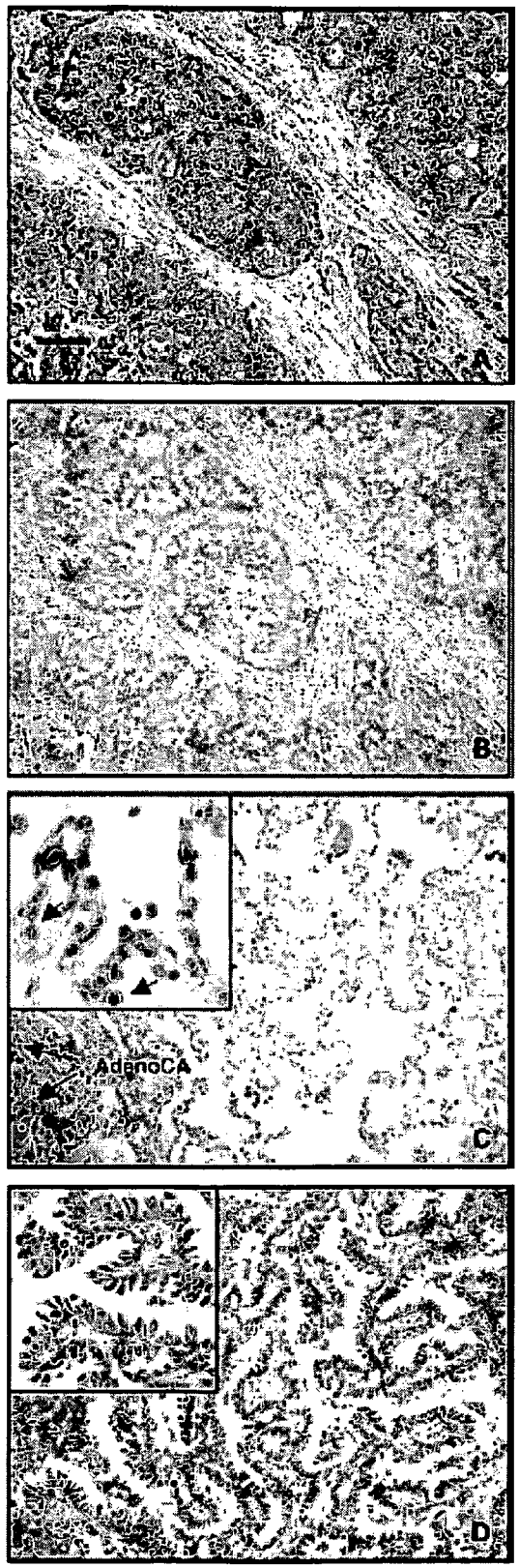

FIG. 6 shows immunohistochemical staining of lung tumor tissues using ENO1 antiserum, as described in Example 6. The arrows indicate increasing reactivity in cytoplasmic, nuclear, or membranous regions in alveolar cells proximate to the tumor. These data show increased ENO1 immunoreactivity in lung tumor samples.

Figure 7A:
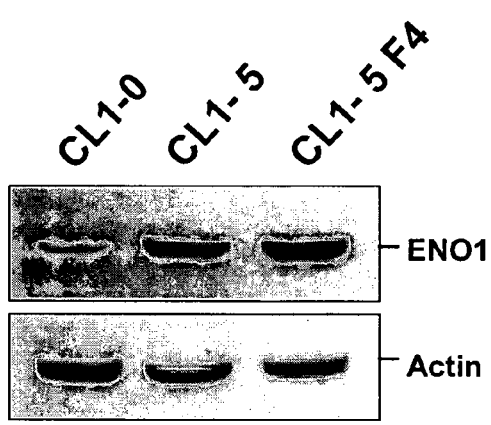

FIG. 7A shows Western blots of human lung cancer cell lines probed with ENO1-specific antibodies, as described in Example 7. Blotting with actin-specific antibodies served as a control. These data show increased expression of ENO1 in CL1-5 and CL1-5F4 cells when compared to CL1-0 cells.

Figure 7B:
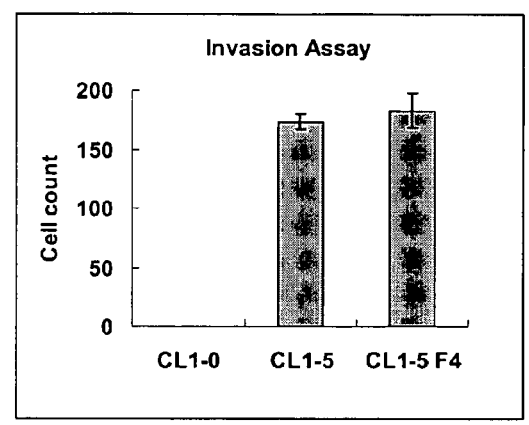

FIG. 7B shows results from Transwell assays showing invasion of human lung cancer cell lines, as described in Example 7. These data show increased invasion of CL1-5 and CL1-5F4 cells compared to CL1-0 cells.

Figure 8:
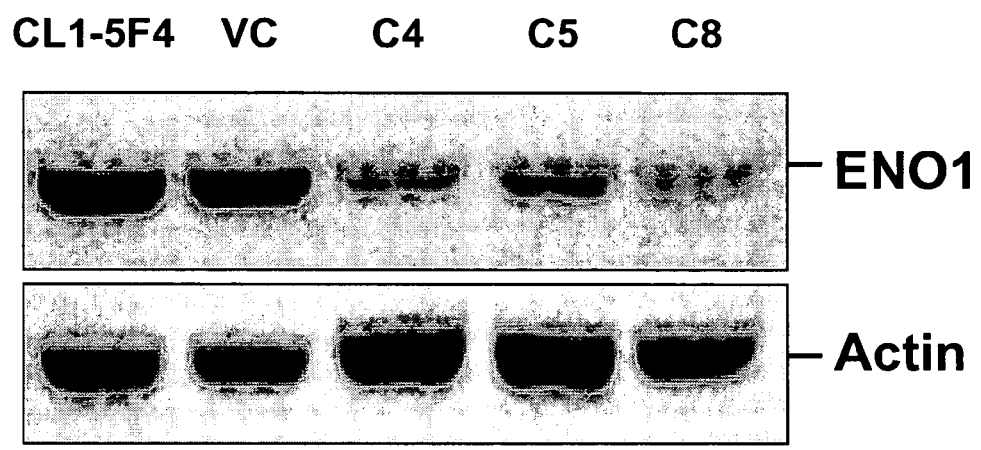

FIG. 8 shows Western blots of cell lysates from human lung cancer cell lines that were transfected with shRNA against ENO1 to specifically knockdown ENO1 expression, as described in Example 8. Blotting with actin-specific antibodies served as a control. These data show that cells transfected with shRNA against ENO1 express lower levels of ENO1 protein.

Figure 9A:
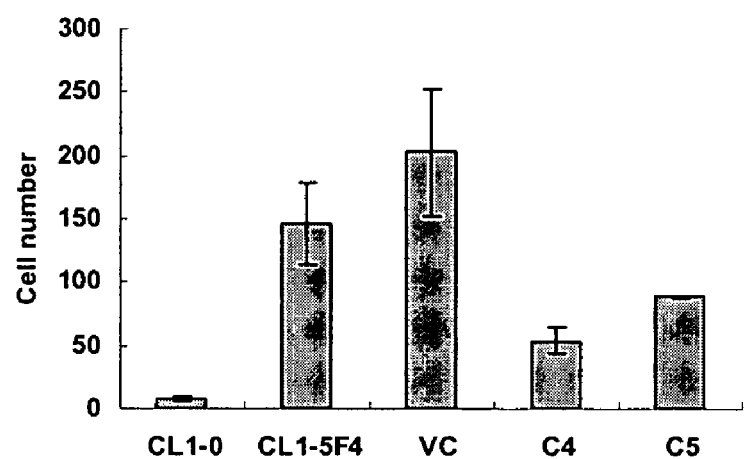
Figure 9B:
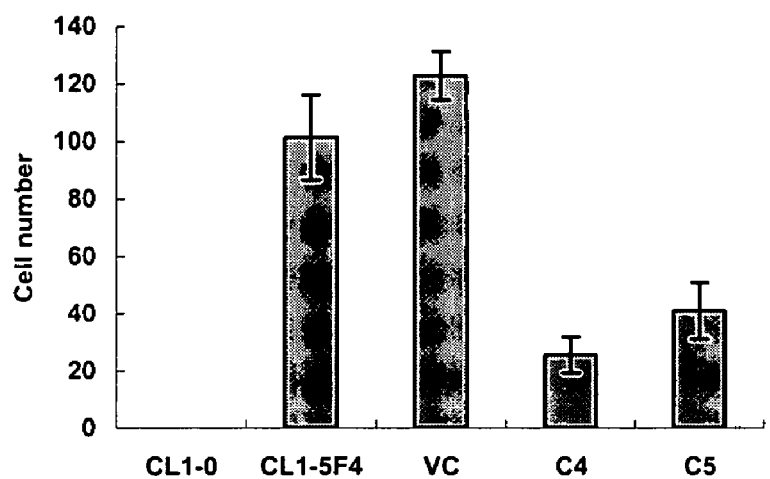

FIGS. 9A and 9B show results from Transwell assays showing cell migration (A) and invasion (B), respectively, of human lung cancer cell lines that were stably transfected with shRNA against ENO1, as described in Example 8. These data show decreased ENO1 expression correlated with decreased cell migration and invasion.

Figure 10:
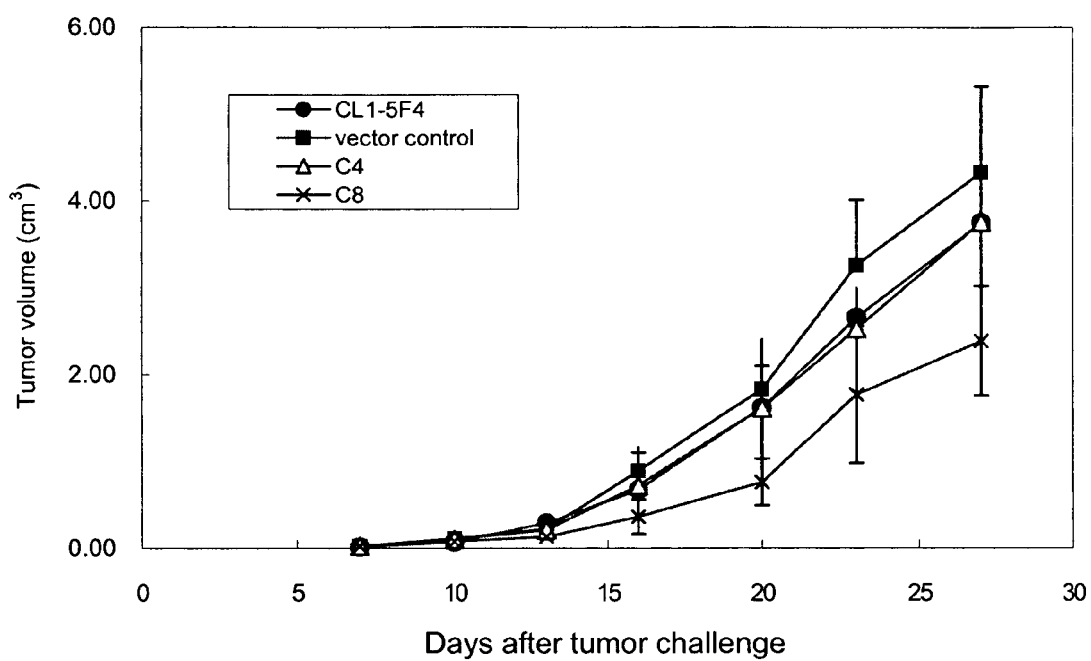

FIG. 10 shows tumor growth in NOD/SCID mice after injection of human lung cancer cell lines that were stably transfected with shRNA against ENO1, as described in Example 8. These data show that decreased ENO1 expression has a minor effect on tumor growth.

Figure 11:
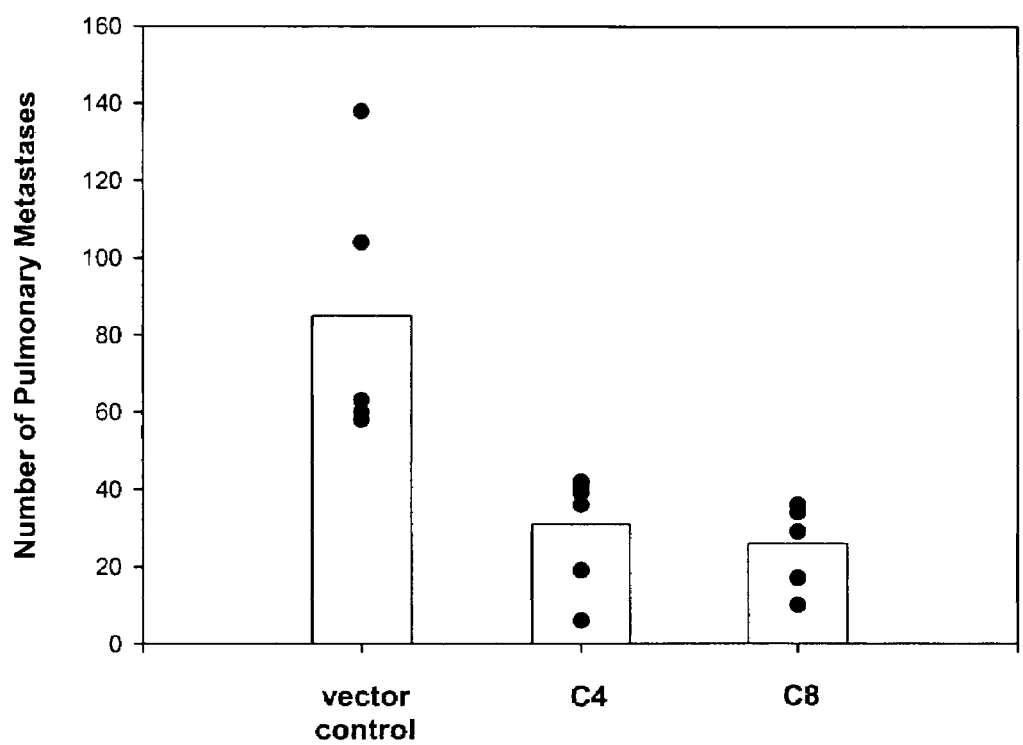

FIG. 11 shows the number of pulmonary metastasis in NOD/SCID mice after injection of human lung cancer cell lines that were stably transfected with shRNA against ENO1, as described in Example 8. These data show that injection of lung cancer cell lines, which were transfected with shRNA against ENO1, generates fewer lung metastasis nodules compared to control cells.

Figure 12:
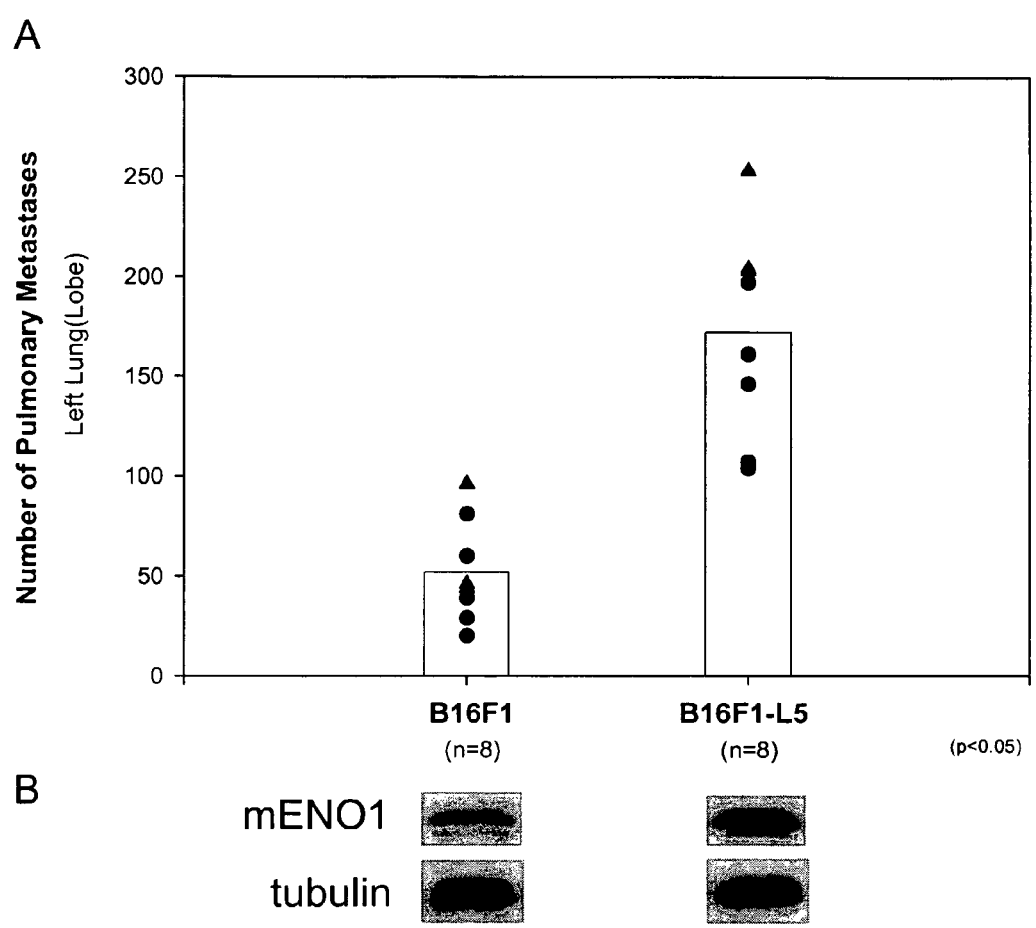

FIGS. 12A and 12B show the number of pulmonary metastasis in C57BL/6 mice after injection of murine melanoma cells and Western blots of ENO1 expression in murine melanoma cells, respectively, as described in Example 8. Blotting with α-tubulin antibodies served as an internal control for Western blots. These data show a correlation between tumor cell ENO1 expression and the number of pulmonary metastases.

Figure 13A:
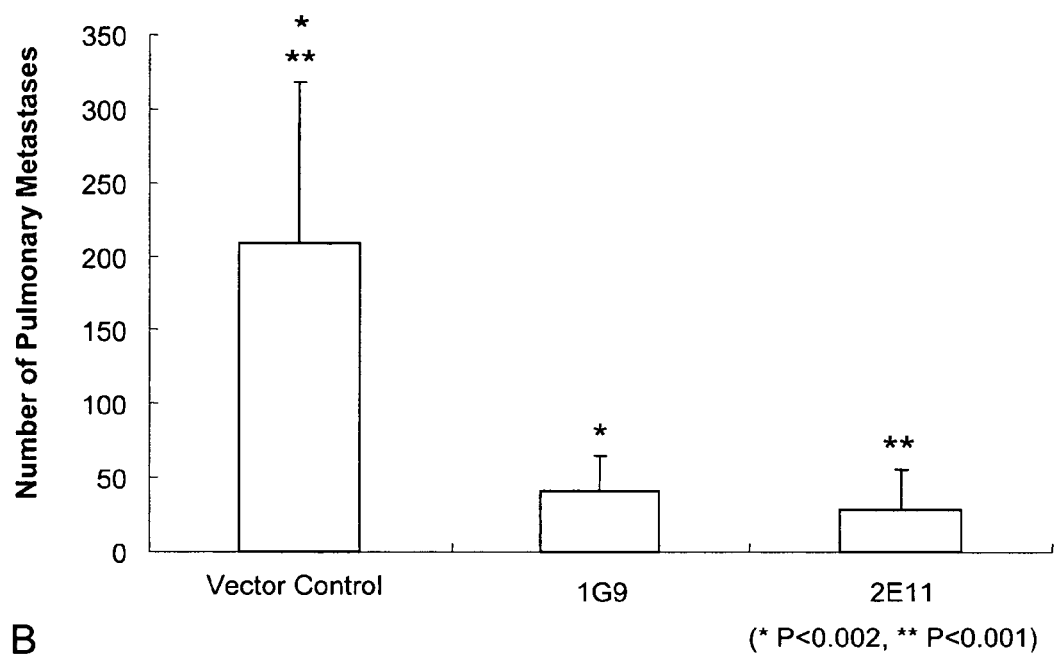

FIG. 13A shows the number of lung tumors in C57BL/6 mice after injection of murine melanoma cells that were transfected with shRNA against ENO1, as described in Example 8. These data show that down regulation of ENO1 expression leads to reduced numbers of lung metastases.

Figure 13B:

FIG. 13B shows Western blots of cell lysates from murine melanoma cells that were transfected with shRNA against mouse ENO1, as described in Example 8. Blotting with α-tubulin antibodies served as a control. These data show that transfecting cells with shRNA against ENO1 lowers ENO1 protein expression.

Figure 14:
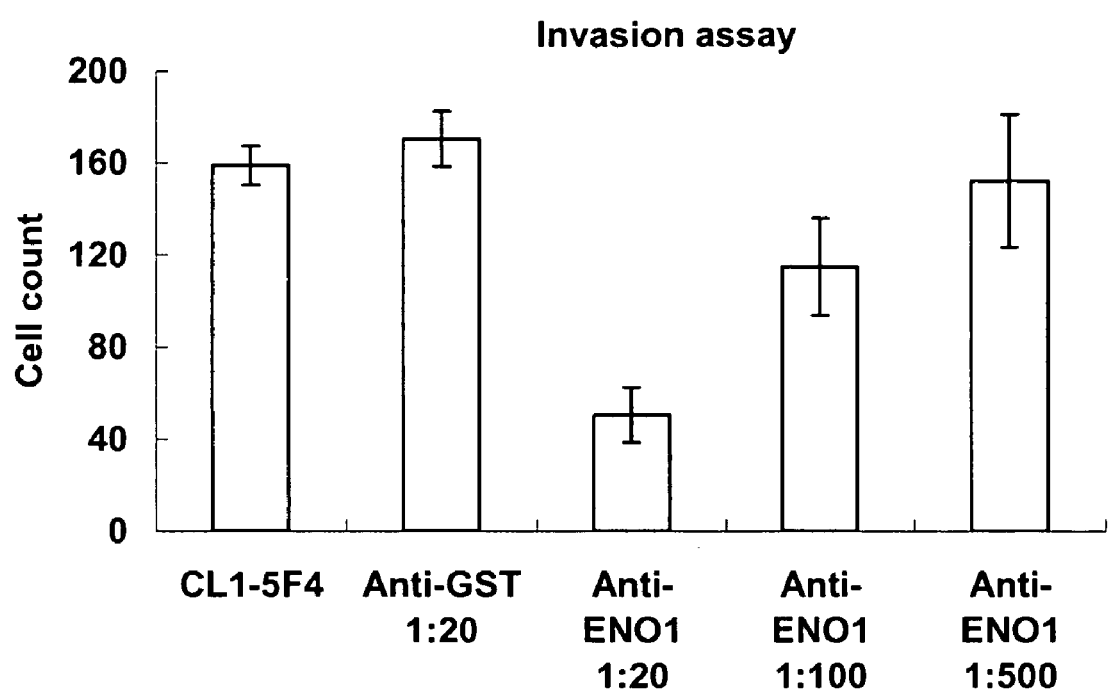

FIG. 14 shows results from Transwell assays demonstrating that ENO1-specific antibody modulates cell invasion, as described in Example 8. These data show that ENO1-specific antibodies decrease tumor cell invasion in a dose-dependent manner.

Figure 15:
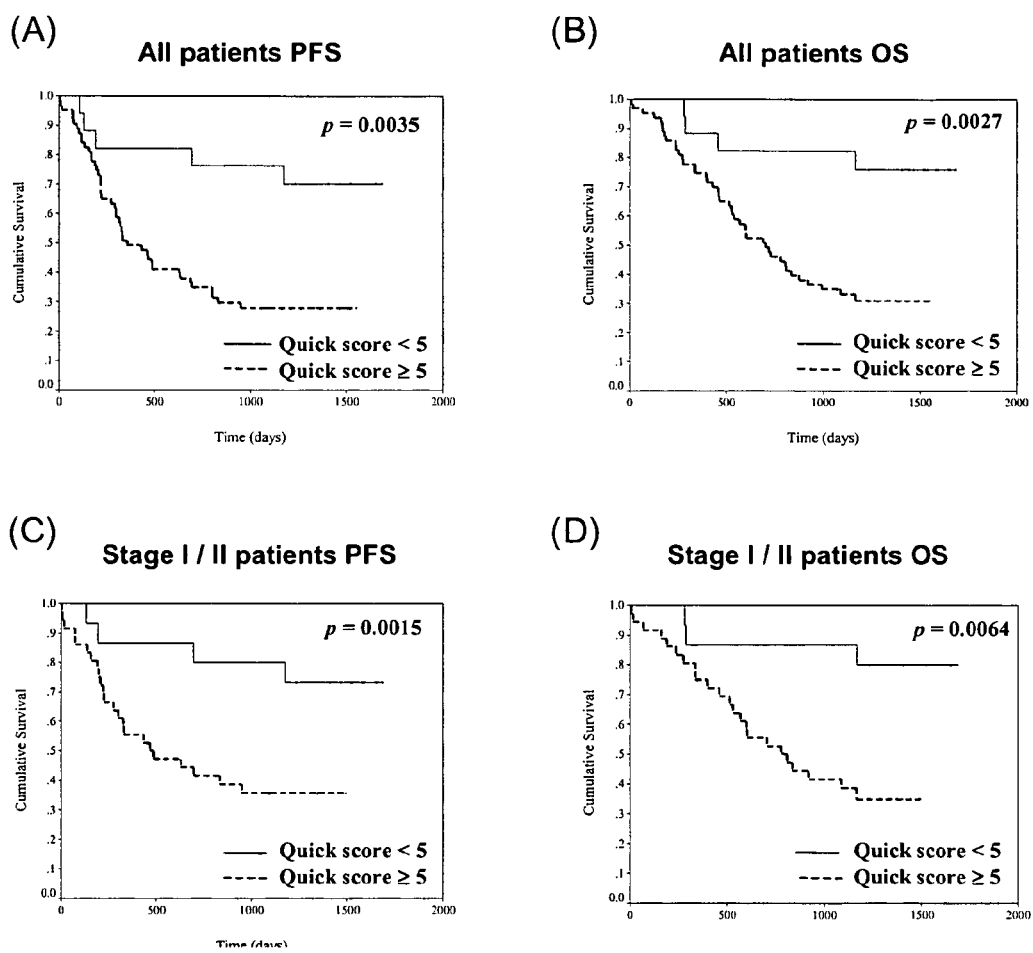

FIG. 15 shows the Kaplan-Meier analysis of progression-free and overall survivals (PFS and OS) in patients with cancer. These results show that higher ENO1 expression in tumors correlates with poor survival, as described in Example 9.

Figure 16:
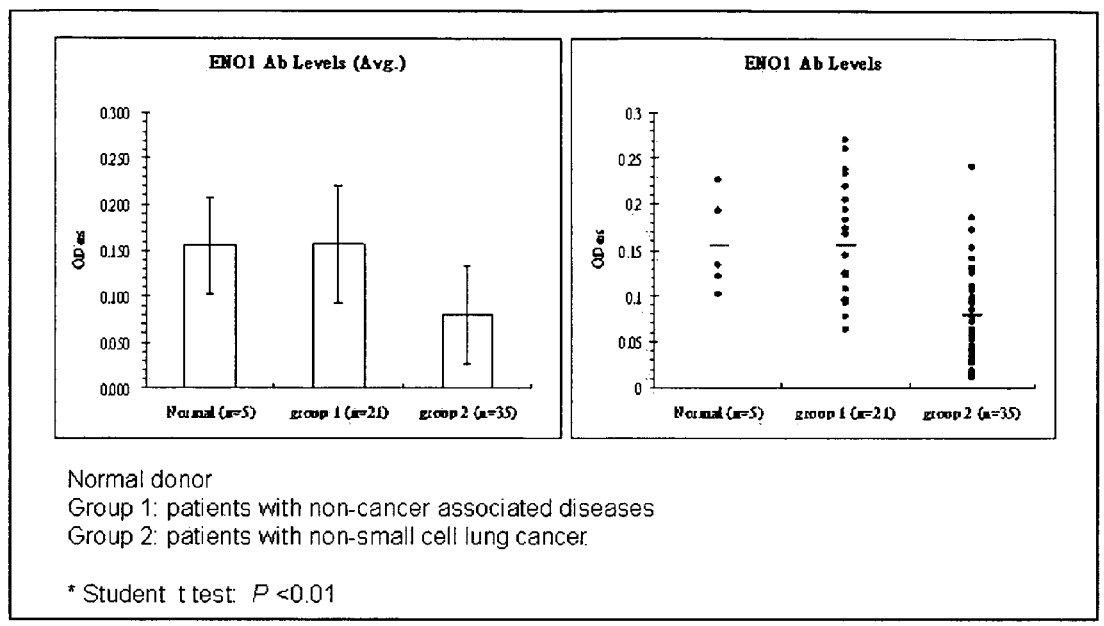

FIG. 16 shows the results of enzyme-linked immunosorbent assays (ELISA) performed with pleural effusions from patients with non-small cell lung cancer (NSCLC), as described in Example 10. These data show lower levels of ENO1 autoantibodies in NSCLC patients compared to healthy donors and patients with non-cancer-associated diseases.

Figure 17:
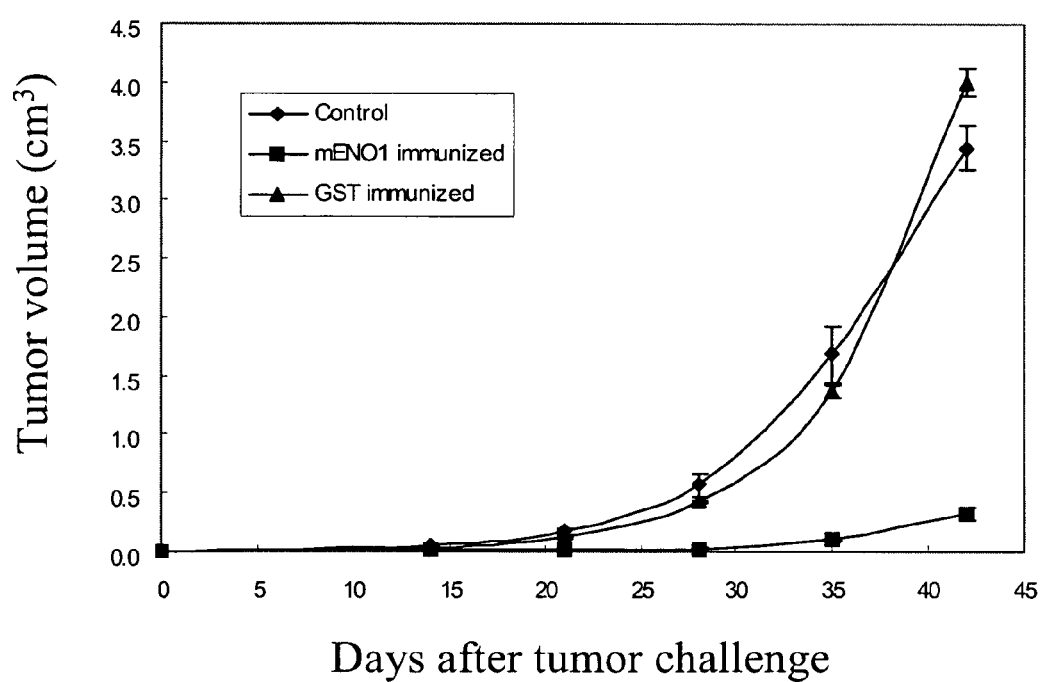

FIG. 17 shows tumor sizes from BalB/C mice that were vaccinated with recombinant ENO1 antigen and challenged with murine hepatoma cells, as described in Example 11. These data show suppressed tumor growth in mice vaccinated with recombinant ENO1.

Figure 18:
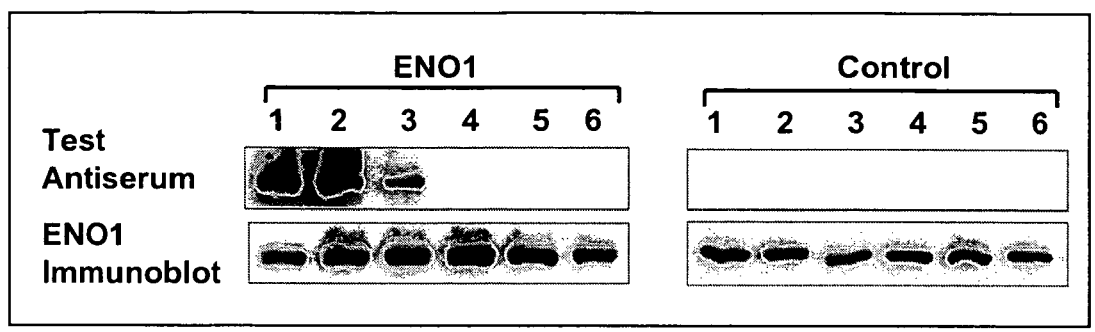

FIG. 18 shows Western blots of ENO1. Blots were probed with serum from BalB/C mice that were inoculated with murine hepatoma cells and challenged with ENO1 antigen, as described in Example 11. These data show that half of the mice (3 out of 6) that were inoculated with murine hepatoma cells and challenged with ENO1 produced detectable ENO1-specific antibodies.

Figure 19:
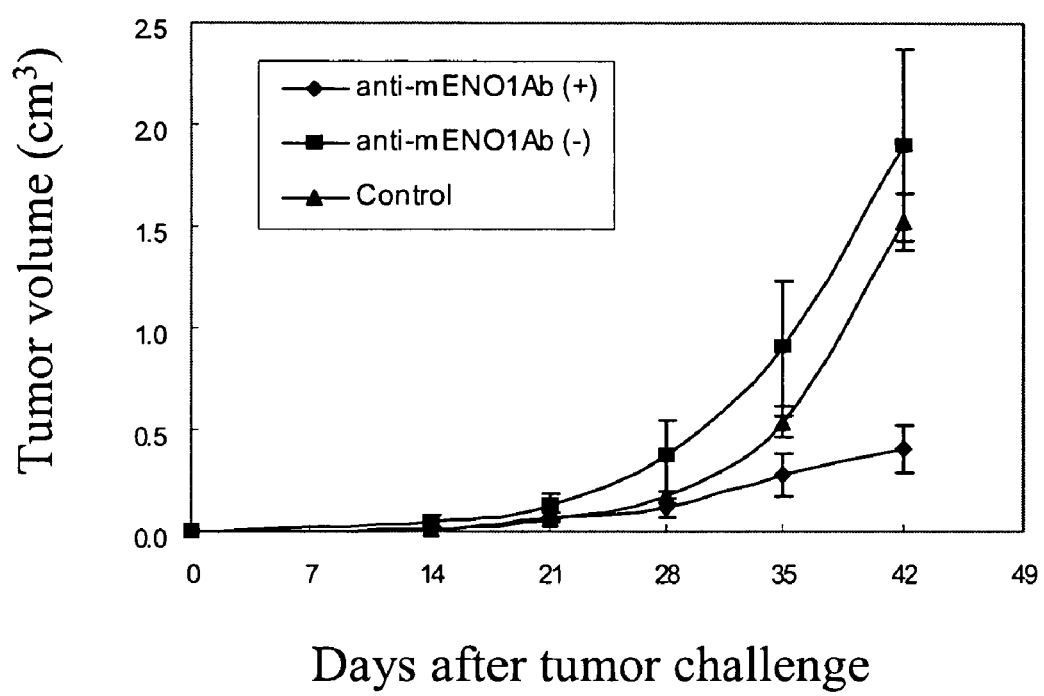

FIG. 19 shows tumor sizes from BalB/C mice that were inoculated with murine hepatoma cells and challenged with ENO1, as described in Example 11. These data show that the mice that produced detectable ENO1-specific antibodies, in FIG. 18, generated smaller tumor sizes compared to mice that did not produce detectable ENO1-specific antibodies.

Table 1 shows the number of patients analyzed in immunohistochemistry (IHC) staining of ENO1 according to staining intensity and distribution, as described in Example 9.

Table 2 shows the correlation expression status of ENO1 and patient-related clinical variables using a Quick score of five as a cutoff value, as described in Example 9.

DESCRIPTION OF THE EMBODIMENTS

In the present invention, a tumor-associated antigen, the p48 antigen, is detected in malignant pleural effusions from patients with lung cancer, using purified lung cancer effusion autoantibodies as probes. The p48 antigen is identified as the human α-enolase (alpha-enolase or ENO1) by biochemical enrichment procedures and mass spectrometric analyses, as described in the Examples section.

The present invention confirms the up-regulation of ENO1 in cancer patients and further provides a method of monitoring cancer development, comprising determining the abundance of alpha-enolase proteins in cancer cells, wherein increased abundance correlates with cancer severity. In one embodiment, in monitoring cancer development, the abundance of alpha-enolase is greater in cancer cells at more advanced stages. In another embodiment, the abundance of alpha-enolase is greater in cells that are likely to exhibit or are exhibiting cancer recurrence. In yet another embodiment, cancer severity relates to survival.

In another embodiment, the abundance is determined by measuring the binding of alpha-enolase specific antibodies to the alpha-enolase proteins. In one embodiment, alpha-enolase antibodies may be induced by injecting animals with the recombinant ENO1 antigen that is purified from *E. coli* transfected with a plasmid containing alpha-enolase cDNA. Alpha-enolase cDNA may be obtained from primers comprising SEQ ID NO: 1 and SEQ ID NO: 2 or degenerate variants thereof. The alpha-enolase specific antibodies may be monoclonal or polyclonal or any other form of antibodies as defined below.

In another embodiment, in monitoring cancer development, abundance is measured by Western blot, surface staining and flow cytometry analysis, immunohistochemistry, quantitative reverse transcriptase-polymerase chain reaction, microarray analysis or any other suitable means that would be known by those of ordinary skill in the art.

Also described is a method of detecting cancer by determining the abundance of ENO1-specific antibodies in a sample, wherein a low level of ENO1-specific antibodies indicates the presence of a malignant tumor. The sample is any sample that contains antibodies, such as a serum sample or pleural effusion sample. A low level of ENO1-specific antibodies refers to the amount of antibodies being statistically significantly lower than healthy people, $p<0.01$. The abundance of the ENO1-specific antibodies can be measured employing the sandwich ELISA method, Western blot, or any other methods known in the art.

In one embodiment, the cancer is non-small cell lung cancer. In one embodiment, the cancer may be non-small cell lung cancer, selected from adenocarcinoma, squamous cell carcinoma, and large cell carcinoma.

The present invention also relates to a method of suppressing tumor growth through inducing anti-ENO1 immune response. The induction of the anti-ENO1 immune response can be carried out through administering ENO1-specific antibodies or ENO1 antigen to the patient. Patients with higher titers of ENO1 antiserum have smaller tumor sizes compared to patients without detectable ENO1 antiserum.

Definitions

As used herein, the term "isolated" or "purified" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "antibody" refers generally and broadly to immunoglobulins, autoantibodies, monoclonal antibodies, and polyclonal antibodies, as well as active fragments thereof. The fragment may be active in that it binds to the cognate antigen, or it may be active in that it is biologically functional. The antibodies of the invention may be chimeric, humanized, or human, using techniques standard in the art.

As used herein, the term "autoantibody" refers to an antibody directed against a self-antigen, i.e, an antibody formed in response to, and reacting against, one of the individual's own normal antigenic endogenous body constituents.

As used herein, the term "monoclonal antibody" refers to antibodies that are chemically and immunologically homogeneous, generally produced by hybridomas. See A Laboratory Manual, Harlow and Lane, eds., Cold Spring Harbor, N.Y. (1988).

As used herein, the term "polyclonal antibody" refers to antibodies that are produced by more than one clone of antibody-synthesizing plasma cells (B-lymphocytes) in response to the same antigen. They are generally produced by the animal after it is immunized with the antigen.

As used herein, the term "chimeric antibody" refers to antibodies that contain sequences from more than one source. For example, such antibodies may contain sequences from non-human sources that are then modified by introducing human sequences).

As used herein, the term "humanized antibody" refers to an antibody in which minimal portions of a non-human antibody are introduced into an otherwise human antibody.

As used herein, the term "human antibody" refers to an antibody in which substantially every part of the protein is substantially non-immunogenic in humans, with only minor sequence changes or variations.

As used herein, the term "alpha-enolase specific antibody" refers to an antibody that has a high specificity for mammalian ENO1 but not to ENO2 or ENO3.

As used herein, the term "ENO1-specific antibody" refers to an antibody that binds to the alpha-enolase protein.

As used herein, the term "recombinant DNA" refers to the nucleic acid sequences that do not occur together in the same arrangement in nature. More specifically, the component sequences are not found in the same continuous nucleotide sequence in nature, at least not in the same order or orientation or with the same spacing present in a recombinant DNA molecule. Standard recombinant DNA and molecular cloning techniques used herein are well known in the art and are described more fully in Sambrook et al. Molecular Cloning: A Laboratory Manual; Cold Spring Harbor Laboratory Press: Cold Spring Harbor, 1989. A "recombinant protein", as the term is used herein, is produced using such recombinant DNA.

As used herein, the term "degenerate variants" refers to any or all nucleic acid sequences that can be directly translated, according to the standard genetic code, to provide an amino acid sequence identical to that translated from a reference nucleic acid sequence or any variations in genetic codes that still maintain the function of the reference nucleic acid.

As used herein, the term "primer" is a polynucleotide chain to which deoxyribonucleotides can be added by DNA polymerase.

As used herein, the terms "effusions" and "effusion" refer to the escape of fluid into a body cavity or tissue, as an exudation or a transudation, for example, pleural effusion and tuberculous pleural effusion.

As used herein, the term "low level" refers to the amount of ENO1-specific antibodies in a patient being statistically significantly lower than that of a healthy patient, $p<0.01$.

As used herein, the term "patient" refers to a mammalian animal, including, but not limited to, human, primates, domestic mammals, laboratory mammals, etc.

As used herein, the term "monitoring" refers to the process of detecting and/or observing the development of cancer by determining the abundance of ENO1 protein in cancer cells.

As used herein, the term "abundance" refers to the expression level of ENO1 in one or more cells. In various embodiments, increased abundance correlates with cancer severity. In other embodiments, abundance is greater in cells at more advanced stages of cancer. In yet other embodiments, abundance is greater in cells likely to exhibit or exhibiting cancer recurrence. In still other embodiments, cancer severity relates to survival.

Methods determining the abundance of ENO1 include, but are not limited to, measuring the binding of ENO1 proteins and ENO1-specific antibodies, Western blotting, flow cytometry, immunohistochemistry (IHC), RT-PCR, and/or microarray analysis.

Lung Cancer Autoantigen/Autoantibody—Alpha-Enolase

In the present invention, a tumor-associated antigen, the p48 antigen, is detected in malignant pleural effusions from patients with lung cancer, using purified lung cancer effusion autoantibodies as probes. The p48 antigen is identified as the human α-enolase (alpha-enolase or ENO1) by biochemical enrichment procedures and mass spectrometric analyses as described in the Examples section.

Enolase was originally characterized as an enzyme involved in glycolytic metabolism but, more recently, accumulating evidence makes clear that enolase is a multi-functional protein (9). In mammalian cells, three isoforms have been found, designated as α- (ENO1), β- (ENO3), and γ- (ENO2) enolases. The expression of these isoforms is developmentally regulated in a tissue-specific manner. ENO1 exists universally in a variety of tissues, whereas ENO2 and ENO3 are exclusively found in neuron/or neuroendocrine and muscle tissues, respectively (10). They form hetero- or homodimers to convert 2-phosphoglycerate into phosphoenolpyruvate in glycolysis.

In addition to the glycolytic function, ENO1 was recently found on cell surfaces and functioned as one of the plasminogen receptors (11), implying that it may play a role in tissue invasion. In a hypoxia situation, ENO1 is one of the stress proteins that is upregulated and is speculated to provide protection to cells by increasing anaerobic metabolism (12). By utilizing an alternative translation start codon, the ENO1 transcript can be translated into a 37 KDa MBP protein, which is localized on the nucleus and is believed to have a function of binding to the c-myc P2 promoter (13).

Development of high-titer autoantibody against enolase has been reported to associate with a diverse range of systemic or organ-specific autoimmune diseases (14). Among these diseases, ENO1-specific autoantibodies have been found in patients with kidney disease, viral hepatitis, systemic lupus erythematosus, etc. However, to the inventors' knowledge, the ENO1 autoantibody has not been identified before in cancer patients despite the fact that ENO2 is already proven to be a product of several types of tumors (15).

Recent studies identified ENO1 as an antigenic target of human oral squamous cancer cells that was recognized by autologous CD4+ T cells (16, 17). The ENO1-specific humoral immunity may be involved in disease malignancy. Presently, cancer-associated retinopathy is the only clinical event found to link with the ENO1 autoantibody. However, mechanisms by which tumor immunity arises and causes visual symptoms remain obscure. Generally, vigorously growing cancer cells or abnormal gene expression (18) is believed to be a potential source of autoantigen inducing this autoimmune disease. The present study has identified ENO1 autoantibodies in cancer patients.

Furthermore, in the present study, a method of producing an ENO1 specific antibody is described. In one embodiment, the method comprises using primers comprising SEQ ID NO: 1 and SEQ ID NO: 2 or degenerate variants thereof, to obtain ENO1 cDNA for cloning; expressing the cloned genes to obtain a recombinant protein, and using the recombinant protein to produce polyclonal antibodies.

In addition, the present study isolated an autoantibody that specifically binds to human ENO1 from the effusion from a cancer patient.

Monitoring Cancer Development Using Alpha-Enolase (ENO1)

Alteration in ENO1 gene regulation has been observed in several types of cancer, but the expression level is quite controversial. Up-regulation of ENO1 at the gene level has been seen in several highly tumorigenic or metastatic cell lines either derived from alveolar type II pneumocytes (19), small cell lung cancer (20), or head and neck cancer (21). Similarly, previous studies on measurement of the enzymatic activities in breast cancer concluded its role in tumor progression (22). One recent bioinformatics study using gene chips and EST databases further supports that ENO1 is ubiquitously overexpressed in 18 out of 24 types of cancer including lung cancer (23).

Genes encoding glycolytic enzymes are critical for cancer cells to adapt to microenvironmental tumor hypoxia. ENO1 is one of the genes up-regulated in response to hypoxia through activation of hypoxia-inducible transcription factor (35). More recently oncogenic AKT and Myc are shown to stimulate aerobic glycolysis (Warburg effect) directly and, ENO1 is one of Myc direct target genes (36). Loss of ENO1 gene regulation has also been detected in some cancers and is highly associated with disease malignancy (19, 20, 23). These data echo Holland (37) and Giallongo's (38) initial observations, showing increased expression of ENO1 in exponentially growing cells but very low levels of ENO1 expression remaining in the cells' resting phase.

However, one recent study on the relationship between ENO1 expression status and clinical outcome displays quite different results. It showed down-regulation of ENO1 was a common theme in patients with non-small cell lung cancer using the 9C12 monoclonal antibody in the study (24). The 9C12 monoclonal antibody, originally developed from Redlitz's lab (11), recognizes both 54- and 48-KDa proteins in U937 lysates and purified human brain ENO1, respectively, implicating the existence of another a-enolase-related molecule (ERM) rather than ENO1. It was also shown not to cross-react with rabbit ENO3 (β-enolase), although its specificity to ENO2 (γ-enolase) has not been defined in any published data. As a matter of fact, ENO2, a neuron-specific enolase, also exists in lung tissue. For example, ENO2 also exists in the CA926 tumor cell in this study. Therefore, the inventors believe that the specificity of antibody to each isoform is a key factor to determine the role of each individual isoforms of enolase in the pathogenesis of a disease.

The present invention confirms the up-regulation of ENO1 in cancer patients and further provides a method of monitoring cancer development, comprising determining the abundance of ENO1 proteins in cancer cells, wherein increased abundance correlates with cancer severity. In one embodiment, in monitoring cancer development, the abundance of ENO1 is greater in cancer cells at more advanced stages. In an embodiment, cancer severity relates to cancer stages. Cancer staging continuously evolves as scientists and physicians learn more about cancer. One current method of cancer staging, the tumor, lymph node, and metastasis (TNM) method, describes the extent of the primary tumor, spread to lymph nodes, and metastasis to other parts of the body. TNM criteria differ based on the type of cancer. General TNM staging definitions are as follows: Stage 0 describes carcinoma in situ (early cancer that is present only in the layer of cells in which it began). Stages I, II, and III reflect the extent of the disease, in terms of greater tumor size, and/or spread of the cancer to nearby lymph nodes, and/or organs adjacent to the primary tumor. Higher stage numbers indicate more extensive disease. Stage IV indicates that the tumor spread to other organs. In another embodiment, the abundance of ENO1 is greater in cells that are likely to exhibit or exhibiting cancer recurrence.

In an embodiment, the abundance is determined by measuring the binding of ENO1 specific antibodies to the ENO1 proteins. Such ENO1 antibodies may be induced, for example, by injecting animals with a recombinant ENO1 antigen that is purified from E. coli transfected with a plasmid containing ENO1 cDNA obtained from primers comprising SEQ ID NO: 1 and SEQ ID NO: 2 or degenerate variants thereof. Such alpha-enolase specific antibodies may be monoclonal or polyclonal or any of the other forms of antibodies described above.

In another embodiment, in monitoring cancer development, abundance is measured by Western blot, surface staining and flow cytometry analysis, immunohistochemistry, quantitative reverse transcriptase-polymerase chain reaction, microarray analysis or any other suitable means that would be known by those of ordinary skill in the art.

Also described is a method of detecting cancer by determining the abundance of anti-ENO1 antibodies in a sample, wherein a low level of the anti-ENO1 antibodies indicates the presence of a malignant tumor. The sample can be any sample that contains antibodies, such as a serum sample or pleural effusion sample. A low level of ENO1-specific antibodies refers to the amount of antibodies being statistically significantly lower than healthy people, $p<0.01$. The abundance of the anti-ENO1 antibodies can be measured employing the sandwich ELISA method, Western blot, or any other methods known in the art.

In these embodiments, the cancer can be non-small cell lung cancer. In one embodiment, it can be non-small cell lung cancer selected from adenocarcinoma, squamous cell carcinoma, and large cell carcinoma. In other embodiments, the cancer is colon cancer, breast cancer or liver cancer.

Functions of ENO1

It is of a general viewpoint that overexpression of glycolytic enzymes, such as ENO1, may enhance aerobic glycolysis of cancer cells and is highly associated with disease malignancy (25). In the present study, rabbit antiserum highly specific to human ENO1 is raised and found to not cross-react with other isoforms. By using this antiserum, the inventors confirmed that ENO1 is significantly overexpressed in effusion tumor cells and tumor parts of lung cancer specimens. Coincidently, its surface distribution was also detected and restricted to tumor cells only. Furthermore, the inventors also determined that the expression level of ENO1 is tightly associated with clinical outcomes in immunohistochemical studies.

Although they do not wish to be bound by this theory, the inventors believe ENO1 has a role in modulating tumor immunity. The presence of humoral immunity against ENO1 in cancer patients may be attributed to an initial overexpression of the antigen during cancer formation followed subsequently by immuno-suppression to facilitate tumor escape. Generally, a primary tumor grows in a microenvironment lacking sufficient nutrient and oxygen supply which results in tumor necrosis. Substantial amounts of ENO1 released from necrotic tumor cells, which overexpress ENO1, may be taken up by antigen-presenting cells and presented to T or B lymphocytes. Autologous CD4+ T lymphocytes recognizing ENO1 as an immunogenic antigen was also recently found in a patient with oral squamous cell carcinoma (17).

Several tumor-associated antigens, in addition to ENO1, are overexpressed in various types of cancers, and they were also proven to have a function on modulation of tumor immunity. These include indoleamine 2,3-dioxygenase (IDO) (39), B7-H1 (40), and RCAS1 (41). B7-H1, for example, is overexpressed in 80-90% patients with a variety of cancers including lung cancer, but has a function to promote apoptosis of tumor-specific cytotoxic T cells leading to tumor escape. However, B7-H1 autoantibodies have not been reported in any cancer yet, and are only found in patients with autoimmune diseases (42).

Similar to B7-H1, overexpression of ENO1 is a common phenomenon existing in not only lung cancers (95%), but also breast (>90%), colon (~40%), and ovary (~30%) cancers in our preliminary studies (data not shown). However, occurrence of ENO1 autoantibodies in pleural effusions from patients with lung cancer is extremely low (7.4%; 3 out of 54), when compared to that of patients with non-cancer associated diseases (54.8%; 17 out of 31). Therefore, the inventors believe that ENO1 has a role in the modulation of tumor immunity.

In addition to the well-characterized glycolytic function of ENO1, it has been reported to participate in other cellular processes such as transcriptional regulation or cell invasion. Several studies have identified the p37 KDa Myc promoter-binding protein-1 (MBP-1), an alternative translation variant of ENO1, as a suppressor for Myc-mediated gene transcription by binding to the P2 promoter of c-myc gene (43). The operation of its function is believed through physical interaction with nuclear histone deacetylase (44). Expression of MBP-1 induces cell death and growth suppression in cell and tumor model (45). However, our ENO1 antiserum did not detect any suspected p37 protein band in Western blotting of the effusion tumor or control cells although the coding sequence of MBP-1 shares 95% of sequence identity with that of ENO1. In the immunohistochemical (IHC) study, some tumor cells (less than 5%) were stained positive in nucleus. Thus, to further verify the identity of the immunoreactive nuclear molecule(s) will be another important issue to distinguish its cellular function from MBP-1. Another putative cellular function of ENO1 is as a plasminogen binding receptor with a suggested role in tissue invasion (11).

Suppression of Tumor Growth

The present invention also relates to a method of suppressing tumor growth in a cancer patient through inducing an anti-ENO1 immune response. The induction of the anti-ENO1 immune response can be carried out through active immunization or passive immunization. Active immunization involves administering ENO1 antigen to a patient while passive immunization involves administering ENO1-specific antibodies to a patient. Patients with higher titer of ENO1 antiserum have smaller tumor size in comparison to patients without ENO1 antiserum.

In various embodiments, ENO1-specific antibodies may be chimeric antibodies. Chimeric antibodies are molecules having different portions derived from different animal species, for example, a variable region derived from a murine immunoglobulin and a human immunoglobulin constant region. They may be used to reduce immunogenicity. Chimeric antibodies and methods for their production are known in the art (Harlow infra; Schrama et al., Nat Rev Drug Discov. 5(2): 147-59 (2006); Liu et al., Proc Natl Acad Sci USA. 84(10): 3439-43 (1987)).

In various embodiments, ENO1-specific antibodies may be humanized or human antibodies. A humanized antibody has one or more amino acid residues from a source which is non-human. Non-human sources may include, but are not limited to, mouse, rat, rabbit, non-human primate or other mammal. Methods for producing and humanizing non-human antibodies and producing human antibodies, can also be used and are well known in the art. Humanized antibodies may be used to reduce immunogenicity, as known in the art (Schrama infra). In yet another embodiment, the antibody may be an active fragment of any of the above.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges including either or both of the upper and lower limits of the range, unless specifically excluded from the stated range.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

The following examples further illustrate the invention. They are merely illustrative of the invention and disclose various beneficial properties of certain embodiments of the invention. The following examples should not be construed as limiting the invention.

EXAMPLES

The practice of the present invention will employ technologies comprising conventional techniques of cell biology, cell culture, antibody technology, and genetic engineering, which are within the ordinary skill of the art. Such techniques are explained fully in the literature.

The following examples illustrate the development and use of ENO1-specific antibodies to monitor cancer development and to detect cancer, as well as suppress tumor growth by inducing an anti-ENO1 immune response.

Example 1

General Methods

Malignant Pleural Effusions and Sample Processing

Malignant pleural effusions were collected and processed for experimental use. Pleural effusions were collected from 54 patients with various subtypes of lung cancer under the permission from IRB, National Health Research Institutes. The 54 patients include 4 patients with small cell carcinoma, 45 patients with adenocarcinoma, and 5 patients with squamous carcinoma. In addition, pleural effusions were also collected from 23 patients with non-cancer associated diseases consisting of pneumonia (12 patients), tuberculosis (5 patients), and heart diseases (6 patients). After collection by thoracocentesis, effusion fluids were promptly centrifuged at 300×g for 10 minutes to pellet effusion cells within 2 hours. Separation of tumor cells from effusion-associated lymphocytes (EALs), to obtain tumor-cell enriched fractions, was performed by a serial gradient centrifugation with Ficoll-Plaque Plus and Percoll (Pharmacia, Uppsala, Sweden) as described previously (26). Cytological examinations were used to estimate the percentage of tumor cells. The purity of tumor cells was between 70% and 90%, as determined by cytologic examinations.

Antibody purification

The immunoglobulins within the tumor-cell enriched pleural effusions were partially purified using ammonium sulfate precipitation. One volume of effusion fluid was added drop wise, with 0.66 volume of ice-cold saturated ammonium sulfate with constant mixing at 4° C. for 1 hour followed by centrifugation at 10,000×g at 4° C. for 10 minutes. The resultant pellet was dissolved in 0.1 volume of distilled water and subsequently dialyzed against phosphate-buffered saline (containing 10% glycerol) overnight. The buffer was then changed, and the sample was again dialyzed overnight.

Immunoblotting

To detect p48, ENO-1, ENO-2, and ENO-3, 50 μg of cell lysates were resolved by 10% SDS-PAGE. The proteins were then detected with appropriate antibodies in Western blotting analyses, as described in each of the following examples. Glyceraldehyde-3-phosphate dehydrogenase (GAPDH) or β-actin served as loading controls. SuperSignal enhanced chemiluminescence (Pierce, Rockford, Ill.) was used to visualize the immunocomplex. The ENO2- and ENO3-specific monoclonal antibodies were obtained from Abnova Co. (Taipei, Taiwan, Republic of China). Myc-tag (9E10), GAPDH, and β-actin were purchased from Upstate Biotechnology (Lake Placid, N.Y.), Biogenesis (Poole, United Kingdom), and Sigma Co. (St. Louis, Mo.), respectively.

Example 2

CA926 Autologous Effusion Antibodies Recognize the p48 Antigen

To detect existing humoral immunity in pleural effusions, 54 lung cancer patients were examined using Western blot analyses of tumor cell-enriched fractions with purified autologous effusion antibodies. Enrichment of effusion-associated tumor cells was performed by serial gradient centrifugations with Ficoll and Percoll as described previously (26). Subsequently, using morphologically normal lung tissues as a control lysate in Western blotting analyses, 4 of 54 patients with antibodies recognized one or two proteins overexpressed or uniquely expressed in the autologous tumor cells. However, no distinct proteins were detected in 21 patients with non-tumor-associated diseases in this screening (data not shown). Patient CA926 is one of the four patients whose effusion antibodies specifically recognize a 48-kDa (p48) major protein in autologous tumor cells. The same antigen appeared in the L89 cancer cell line. The antigen identity was confirmed by a competition experiment using CA926 effusion antibodies preabsorbed with the L89 lysate. Therefore, L89 was used as the source for the protein identification in this study.

Specifically, thirty micrograms of p48-enriched lysate from CA926 and L89 cells were electrophorized and immunoblotted with CA926 antibodies. In addition, CA926 lysate was immunblotted with CA926 antibodies after absorption with immobilized L89 lysate. The immunoreactions were carried out in an incubation manifold (Hoefer, San Francisco, Calif.). GAPDH was used as a protein loading control. Molecular weight markers (kDa) are shown on the left.

Figure 1:
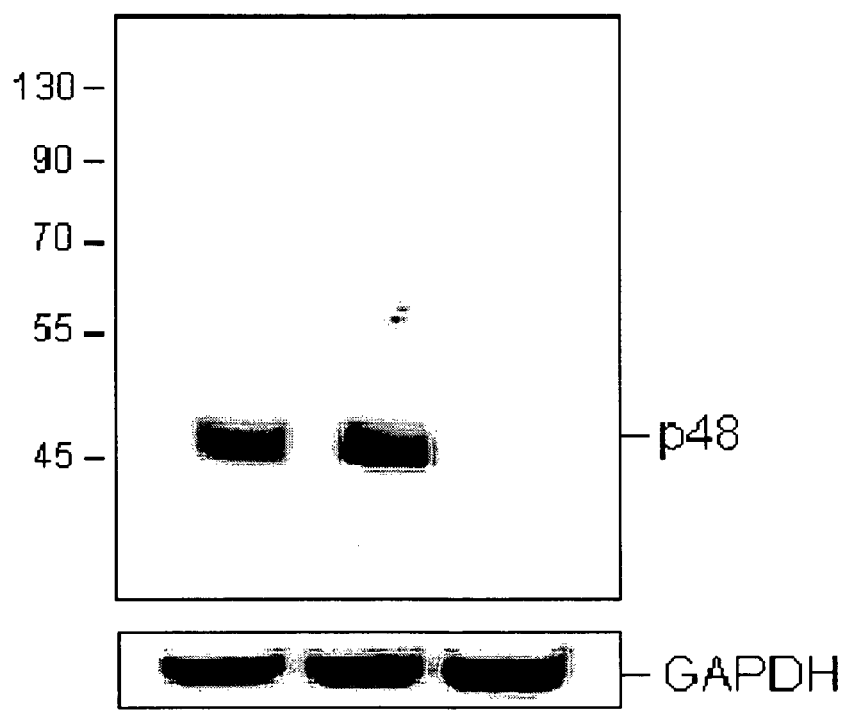
FIG. 1 shows Western blots of p48-enriched cell lysates probed with CA926 antibodies or the antibodies preabsorbed with immobilized L89 lysate according to Examples 1 and 2. These experiments show that the p48 antigen is the major immunoreactive target of CA926 effusion antibodies in CA926 and L89 tumor cells.

The results of this experiment are shown in FIG. 1. Both tumor cells from CA926 and L89 contained antigens recognized by the antibodies purified from the CA926 pleural effusion. The preabsorption experiment shows that the antigen in CA926, which is recognized by the CA926 antibody, is also found in L89. The molecular weight of the recognized antigen suggests that the CA926 antibody recognizes the p48 antigen.

Example 3

Purification and Identification of the p48 Antigen

Identification of the p48 Antigen

Identification of the p48 antigen was done by biochemical purification and mass spectrometry analysis. Biochemical purification of the p48 antigen was carried out by performing three steps: (1) DEAE chromatography purification, (2) ammonium sulfate precipitation, and (3) SDS-PAGE separation. Detergent-soluble L89 lysate was dialyzed and precleared by centrifugation before purification.

Figure 2A:
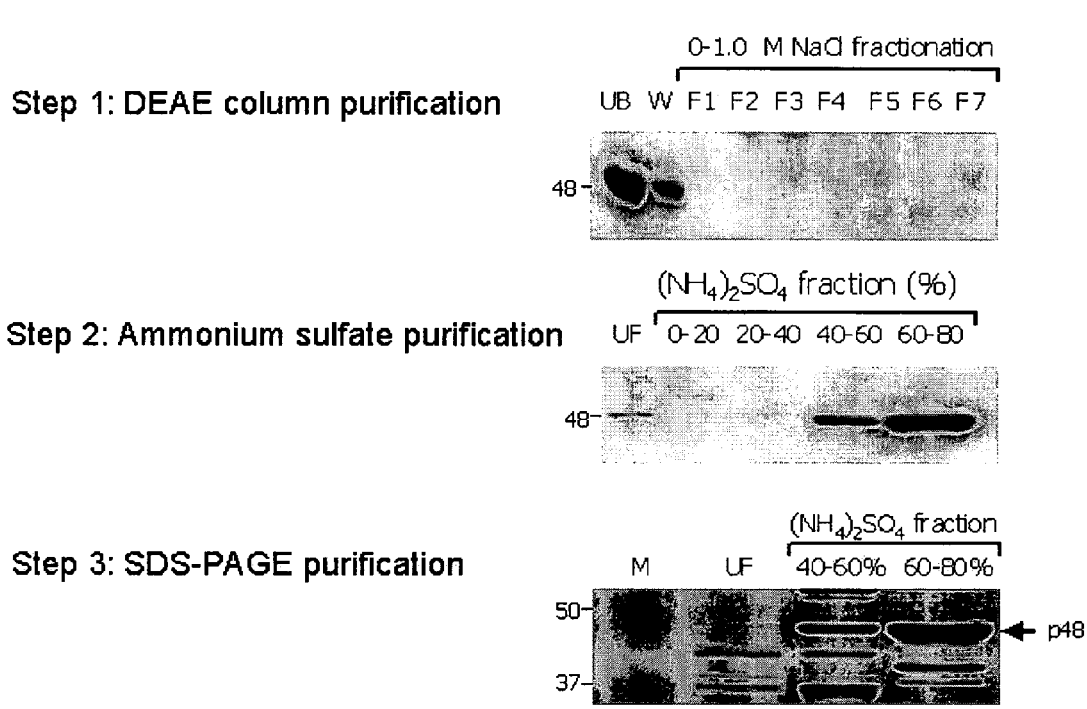
FIG. 2A shows Western blots of L89 lysates during p48 antigen purification. DEAE column purification, ammonium sulfate purification, and SDS-PAGE purification were performed as described in Example 3. These data show that the p48 antigen was purified from L89 cells.

Results from step 1 are shown in FIG. 2A. Lysates were loaded onto a DEAE column. The bounded proteins were fractionated by increasing concentration of NaCl. The DEAE column buffered with 20 mmol/L Tris-HCl (pH 7.0) optimally bound 94.6% of loaded proteins but excluded the p48 from the column. Western blotting of unbound (UB), washout (W) lysates, and fractionated elutants (F1-F7), probed with CA926 effusion antibodies, shows the presence of the antigen in unbound (UB) and washout (W) fractions.

Results from step 2 are shown in FIG. 2A. The UB and W fractions containing p48 subsequently were fractionated with increasing fractions of saturated, ice-cold ammonium sulfate (ranging from 0% to 80%). Western blotting with CA926 antibodies demonstrated that the antigen was concentrated primarily in the 60% to 80% fraction.

Results from step 3 are shown in FIG. 2A. Ammonium sulfate-fractionated lysates were resolved on 10% SDS-PAGE in duplicate. One was probed with CA926 antibodies while the other was visualized by silver staining. The putative immunoreactive protein band in the gel was excised for mass spectrometry analysis.

Figure 2B:
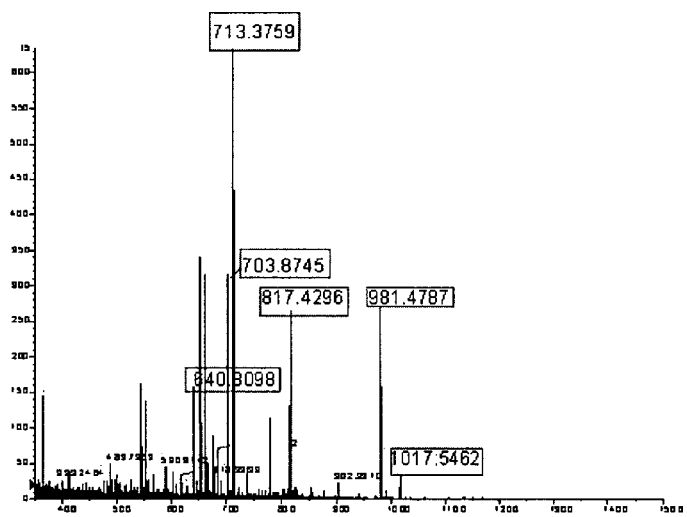
FIG. 2B shows the results of mass spectrometry analysis of purified p48. The p48 protein bands from FIG. 2A were trypsinized and sequenced. The peptide sequences correspond to human α-enolase in the NCBI protein database, as described in Example 3. These data show that the p48 antigen is ENO1.

Results from mass spectrometry analysis are shown in FIG. 2B. MALDI-MS spectrum was obtained from trypsinized p48 protein bands (Matrix Science, Co). Six randomly chosen peptides (framed) were sequenced. The peptide sequences that corresponded to human a-enolase are listed at the bottom of FIG. 2B.

Confirmation of the Identity of the p48 Antigen

Figure 2C:
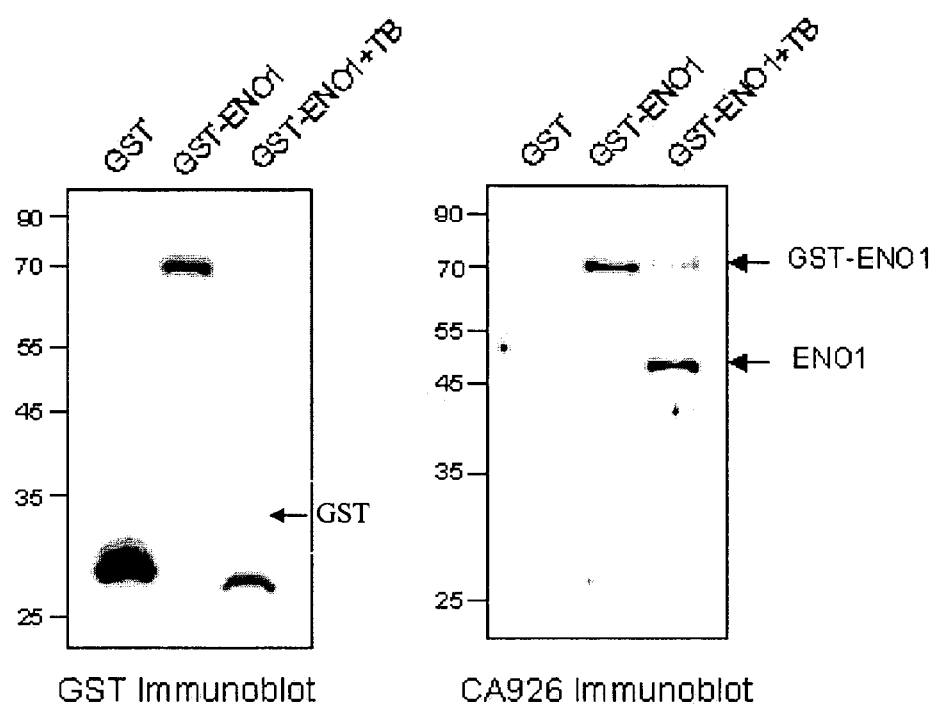
FIG. 2C shows Western blots of ENO1 that was cloned from L89 cells. GST-ENO1 was treated with thrombin prior to Western blotting where indicated. Blots were probed with either GST or CA926 antibodies, according to Example 3. These data confirm that ENO1 is the immunoreactive target of CA926 effusion antibody.

Further studies were carried out to confirm that ENO1 is the target of CA926 antibodies. Experiments were performed using recombinant ENO1 protein. To generate recombinant α-enolase (ENO1) protein, the ENO1 gene was cloned out from NHRI-L89 cells by reverse transcriptase-PCR (RT-PCR) using gene-specific primers: (1) forward: 5'-GGTG-GAATTCTATCTATTCTCAAGATCCAT-GCC-3' (SEQ ID NO: 1) and (2) reverse: 5'-ACTCCATGGTTACTTGGC-CAAGGGGTTTCT-3' (SEQ ID NO: 2), digested with EcoRI and NcoI, cloned into pGEX-KG vector, and expressed in *Escherichia coli* cells to generate a GST-tagged recombinant protein. Protein purification was performed using glutathione-immobilized affinity chromatography, as recommended by the manufacturer (Sigma, St. Louis). The GST tag protein was then removed by thrombin enzymatic digestion. Western blotting of one microgram of GST-tagged protein and ENO1 recombinant protein (GST-ENO1) with or without thrombin (TB) treatment was conducted with either GST or CA926 antibodies as indicated at the bottom of FIG. 2C. The Western blot result in FIG. 2C shows that CA926 antibodies specifically recognize ENO1 and its fusion protein, but not GST. These data show that ENO1 is the antigenic target of the CA926 tumor cells.

Example 4

Isoform-Specific Recognition by CA926 Antibodies

The three mammalian isoforms of enolase, α-(ENO1), β-(ENO3), and γ-(ENO2) isoforms, share around 84% protein sequence identity. Therefore, studies were carried out to determine the presence of these isoforms in CA926 and L89 tumor cells.

RT-PCR

Figures 3A, 3B:
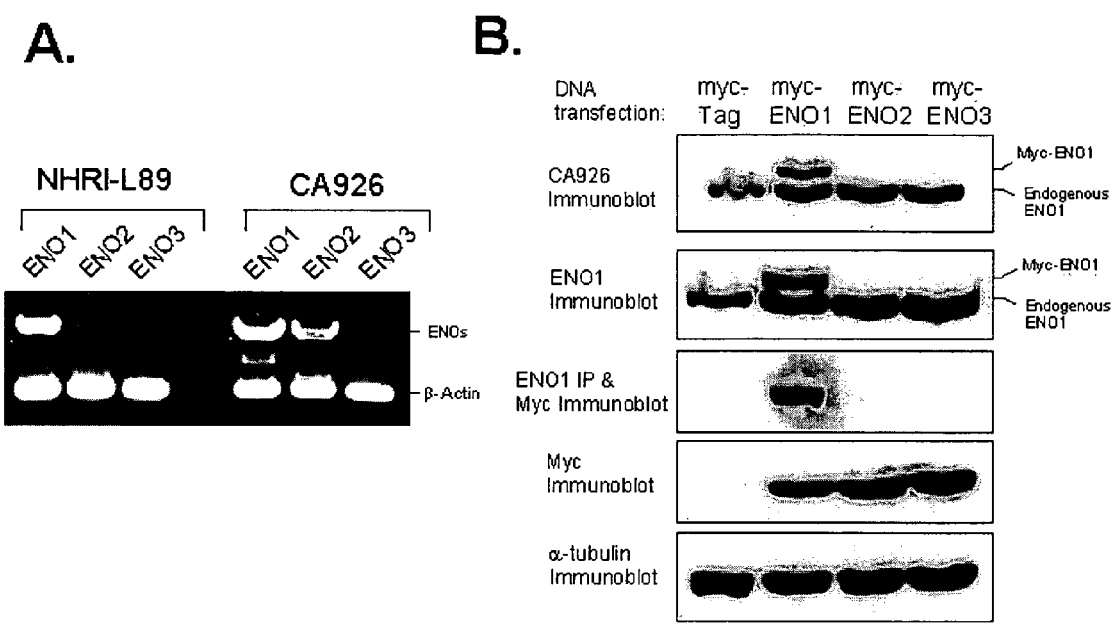
FIG. 3A shows the results of reverse transcription polymerase chain reactions (RT-PCR) designed to detect ENO1, ENO2, and ENO3 in L89 cells and CA926 tumor cells, according to Example 4. RT-PCR using primers specific to β-actin served as an internal control. These data show that L89 cells express ENO1, but not ENO2 or ENO3. These data also show that CA926 cells express ENO1 and ENO2, but not ENO3.
FIG. 3B shows Western blots of transfected HeLa cell lysates. HeLa cells were transfected with Myc-tagged ENO1, ENO2, ENO3, or empty vector prior to lysis. Transfected HeLa cell lysates were hybridized with ENO1 antiserum and probed for Myc-tagged proteins, according to Example 4. These data show that ENO1 antiserum specifically recognizes ENO1.

To investigate the specificity of CA926 effusion antibodies, the genes encoding ENO2 and ENO3 were cloned out from CA926 and human heart cDNA pools, respectively. Human β(ENO3)- and γ(ENO2)-enolase genes were cloned from human heart (Strategene, La Jolla, Calif.) and CA926 cDNA pools, respectively, by RT-PCR. The isoform-specific primers used for the gene cloning are listed as follows: ENO2 forward: 5'-ATTGAATTCTTCCATAGAGAA-GATCTGGGCCCGG-GAGAT-3' (SEQ ID NO: 3) and reverse: 5'-ATTGAATTCTCACAGCACACTGGGAT-TACGGAAG-3' (SEQ ID NO: 4); ENO3 forward: 5'-AGGG-AATTCTGCCATGCAGAAAATCTTTGC-3' (SEQ ID NO: 5) and reverse: 5'-ATTGAATTCTCACTT-GGCCT-TCGGGTT-3' (SEQ ID NO: 6). The resultant fragments were digested with EcoRI, cloned into pBlueScript-myc vector, and over-expressed in HeLa cells by infection of T7 vaccine viruses as described previously (32). To generate Myc-tagged recombinant ENO1 protein, ENO1 gene was cloned out from NHRI-L89 cells by reverse transcriptase-PCR (RT-PCR) using gene-specific primers: (1) forward: 5'-GGTGGAAT-TCTATCTATTCTCAAGATCCAT-GCC-3' (SEQ ID NO: 1) and (2) reverse: 5'-ACTCCATGGTTACTTGGC-CAAGGGGTTCT-3' (SEQ ID NO: 2). Results from RT-PCR analysis are shown in FIG. 3A. These results demonstrate that CA926 cells express ENO1 and ENO2, but not ENO3; whereas L89 cells predominantly express ENO1. β-actin was included in the reactions as an internal control.

Immunoblotting and Immunoprecipitation

ENO1-specific antiserum was raised by immunizing rabbits with the recombinant GST-ENO1 protein generated, as described above, by Kelowna Inc. (Taipei, Taiwan). To avoid cross-reaction, the serum was further absorbed with immobilized GST-resin and the lysate of *E. Coli* which expressed the GST-tagged protein, prior to use. The specificity of the rabbit anti-serum to individual isoforms of enolase was examined by Western blotting and immunoprecipitation. The ENO2- and ENO3-specific monoclonal antibodies were obtained from Abnova Co. (Taipei, Taiwan, ROC).

Seventy micrograms of ENO1-, ENO2-, or ENO3-transfected HeLa lysates were resolved on 10% SDS-PAGE and blotted with antibodies. For the immunoprecipitation (IP) experiment, transfected HeLa cell lysates were hybridized with ENO1 antiserum, precipitated with protein-G beads (Pierce, Rockford, Ill.), and probed for Myc-tagged proteins for immunoprecipation experiments.

Results from the above experiments are shown in FIG. 3B. Antibodies or antisera used for blotting are indicated on the left side of FIG. 3B. Endogenous ENO1 and Myc-tagged ENO1 are indicated on the right side of FIG. 3B. CA926 antibodies recognized endogenous ENO1 in ENO1-, ENO2-, ENO3-, and empty vector-transfected HeLa cells. CA926 antibodies also recognized recombinant Myc-tagged ENO1 in ENO1-transfected HeLa cell lysates. Blots using anti-Myc antibodies or anti-α-tubulin antibodies served as controls. Blotting with antibodies specific to ENO1, ENO2, or ENO3, confirmed that the transfected cells expressed the appropriate enolase isoforms. The IP experiment confirmed that the ENO1-specific antibody specifically recognized ENO1. These results demonstrate that CA926 antibodies and the rabbit anti-ENO1 antiserum recognize ENO 1, but do not recognize ENO2 or ENO3.

Example 5

Low Frequency of ENO1-Specific Antibodies in Patients with Cancer

Western blots were performed to determine the occurrence of ENO1-specific antibodies in effusions from patients with cancer and patients with non-cancer associated diseases. ENO1-specific antibodies were detected in 3 out of 54 cancer patients and 17 out of 31 patients with non-cancer-associated diseases.

Figures 4A, 4B:
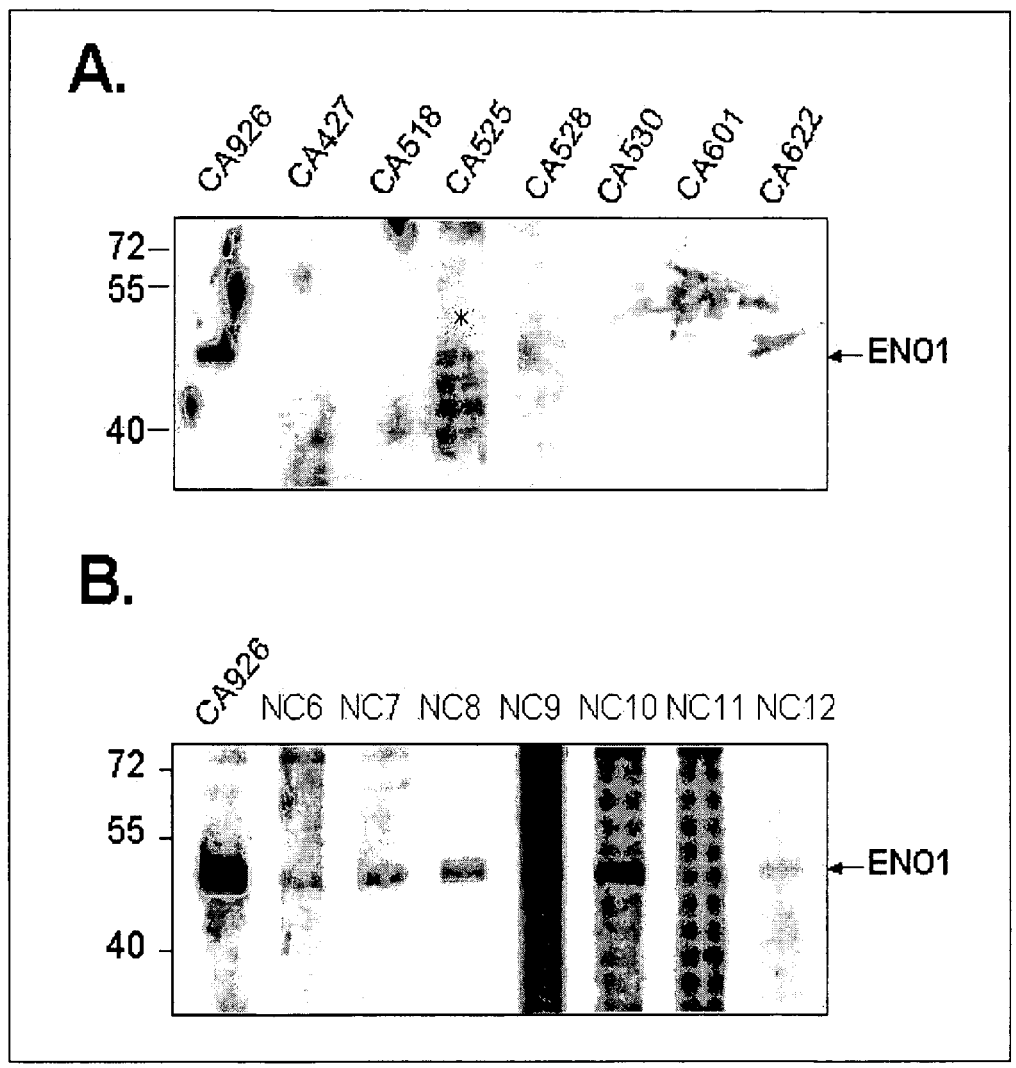
FIGS. 4A and 4B show Western blots of ENO1 probed with pleural effusion antibodies from patients with non-small cell lung cancer (NSCLC) (A) and from patients with non-cancer-associated diseases (B), according to Example 5. These data show a greater occurrence of antibodies that recognize ENO1 in patients with non-cancer-associated diseases compared to patients with cancer.

Results from these experiments are shown in FIGS. 4A (patients with cancer) and 4B (patients with non-cancer associated diseases). These results indicate that ENO1-specific antibodies are detected less frequently in patients with cancer compared to patients with non-cancer associated diseases. The asterisk in FIG. 4A indicates the weaker immunoreactivity detected in this experiment, suggesting that ENO1 mediated immuno-modulation probably occurred in most of the cancer patients. The data shown in FIGS. 4A and 4B are 8 representative individuals from 54 patients with lung cancer and 7 representative patients from 31 patients with non-tumor associated diseases, respectively. These results suggest that ENO1-mediated immunomodulation likely occurred in most of the cancer patients.

The levels of ENO1 antibodies in patients with lung cancer and non-cancer associated diseases or in healthy subjects were determined by a sandwich-ELISA. Purified GST-tagged ENO1 protein or GST protein (0.2 μg/well) was bound using immobilized GST monoclonal antibodies (Pierce) on each well of 96-well plates. Diluted sera or effusions (1:10 dilution) obtained from healthy subjects or patients were used to estimate the levels of ENO1 antibody in each patient. Sera or effusions were probed with anti-human IgG conjugated with HRP (Jackson Lab) and visualized with ABTS HRP substrate (KPL, Gaithersburg, Mass.) at $OD_{405}$. The levels of ENO1 antibody were determined by comparing the reading at $OD_{405}$.

Figure 4C:
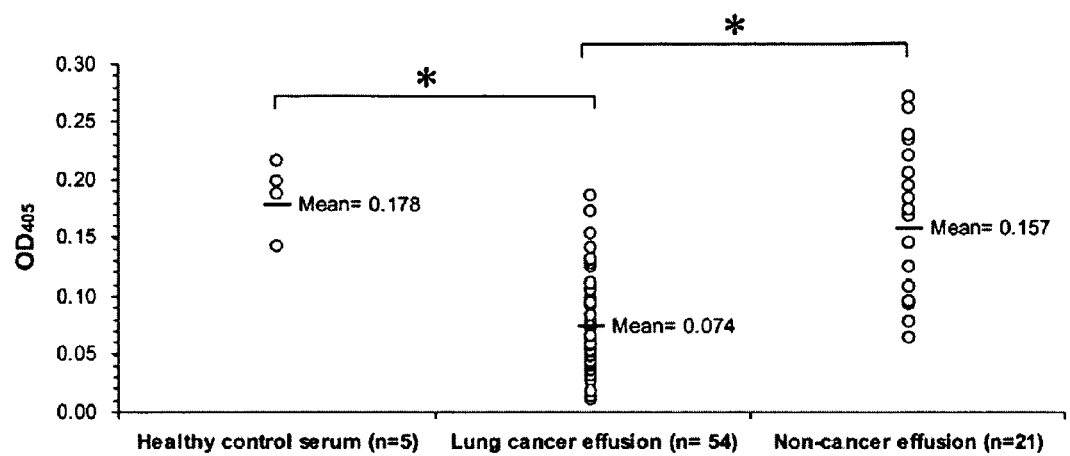
FIG. 4C shows the results of enzyme-linked immunosorbent assays (ELISA) performed with serum from healthy
} individuals, pleural effusion from patients with non-cancer-associated diseases, and patients with NSCLC cancer, according to Example 5. These data show higher levels of ENO1-specific antibodies in patients with non-cancer-associated diseases and healthy individuals compared to patients with NSCLC cancer.

Results from the ELISA analyses are shown in FIG. 4C. The asterisk indicates statistical significance using the Student T-test (P<0.01). The mean ENO1-specific antibody level from healthy control serum was not statistically different from the mean ENO1-specific antibody level from non-cancer effusion. The mean levels from healthy control serum and from non-cancer effusion were each statistically significantly different from the mean level from lung cancer effusions (P<0.01, in each case). The experiments demonstrate significantly lower levels of anti-ENO1 autoantibodies in patients with cancer compared to those in patients with non-cancer-associated diseases and healthy subjects.

Example 6

Overexpression of ENO1 in Lung Tumor Cells and Tissues

ENO1 antiserum immunoblotting, ENO1 surface staining, and immunohistochemistry (IHC) were used to determine whether ENO1 is abnormally expressed in tumor cells. Two types of human lung primary cells, normal human bronchial epithelial (NHBE) and small airway epithelial (SAEC) cells, were used as controls. Data from Western blotting and IHC studies indicate that ENO1 is upregulated in patients with lung cancer.

ENO1 Antiserum Immunoblotting

To determine ENO1 expression levels, 17 of 54 patients with lung cancer and 6 of 21 patients with non-cancer-associated diseases containing sufficient amount of effusion cells, were examined. L89, CA926, CA1207, and CA2730 are cells from patients with lung cancer while NC13 and NC16 are cells from patients with non-cancer-associated diseases. Lung embryonic epithelial cells (WI38 cells), normal human bronchial epithelial (NHBE) cells, and small airway primary epithelial (SAEC) cells, were used as controls and were purchased from Cambrex (Walkersville, Md.). Control cells were cultured in appropriate media, provided by the manufacturer, for two passages. Thirty micrograms of cell lysate was resolved on 10% SDS-PAGE and immunoblotted with ENO1 antiserum. Blotting with β-actin-specific antibodies served as an internal control.

Results from these experiments are shown in FIG. 5A. ENO1 antiserum recognized two-fold more ENO1 protein in L89, CA926, CA1207, and CA2730 cells compared to NHBE, SAEC, NC13, and NC16 cells. Thus, ENO1 was overexpressed in cells from patients with lung cancer compared to non-cancer cells.

ENO1 Surface Staining and Flow Cytometry

Cells

The effusion primary tumor cell obtained from a 51 year-old female patient with lung adenocarcinoma, line CA926, was grown in DMEM supplemented with 10% fetal bovine serum (FBS) (Hyclone, Logan, Utah), 1 mM sodium pyruvate (Introgen, Grand Island, N.Y.), 0.1 mM non-essential amino acid (Sigma-Aldrich, St. Louis), 2 mM glutamine, 50 μg/ml streptomycin, and 500 U/ml penicillin, for two passages in vitro. The NHRI-L89 cell line was originally obtained from effusion tumor cells of a 36 year-old female patient with stage IV lung adenocarcinoma and characterized as cytokeritin (+)/ calretinin (−). The cells were cultured in RPMI1640 medium supplemented with 5% fetal bovine serum, 2 mM glutamine, and antibiotics, for at least 40 passages in vitro.

Surface Staining and Flow Cytometry

For flow cytometric analysis, cells isolated from cancer- or non-cancer-associated effusion fluids were cultured in ACL-4 (27) and RPMI-1640 media (1:1) for one or two passages depending on the cells. The intact whole cells were stained with or without ENO1 antibody (1:300 dilution), visualized with Cy2-conjugated goat antiserum (Jackson Lab), and analyzed with FACScan flow cytometer (Becton Dickinson). ENO1 expression is measured by the resulting fluorescence intensity.

Results from these experiments are shown in FIG. 5B. The histograms generated from incubating NHBE and SAEC cells with or without the ENO1 antibody are indistinguishable, indicating that these cells do not express detectable levels of ENO1 on the cell surface. Incubating L89 and CA926 cells with ENO1 antibodies shifts the histogram to the right compared to incubating the cells without ENO1 antibodies, indicating that L89 and CA926 cells express ENO1 on their cell surfaces. These data support previous studies that ENO1 has a role in metastasis (11).

Immunohistochemistry

Tissue Sample Preparation and Clinical Characterization of Patients

The acquisition of paraffin tissues was approved by local Institutional Review Boards. Formalin-fixed, paraffin-embedded tissue samples were obtained from 80 patients with non-small cell lung cancer (NSCLC), including 40 patients with squamous cell carcinoma (SCC), 31 patients with adenocarcinoma (AD), 4 patents with adenosquamous cell carcinoma, and 5 patients with large cell carcinoma. The histology of tumor types was determined according to WHO classification, and disease stages were adjudged by tumor size and node metastasis. No patients received adjuvant or neo-adjuvant therapy. Surgery was performed from January 2000 to December 2001 with complete follow-up at Taichung Veterans General Hospital.

Immunohistochemistry Staining

To determine the expression of ENO1 in lung tumors, immunohistochemical (IHC) study was performed in 80 samples, using a conventional method. Briefly, tissue sections (4 μm thick) were mounted on poly-L-lysine-coated slides, air-dried, and deparaffinized. Endogenous peroxidase activity was blocked with 0.35% hydrogen peroxide in 50% methanol for 30 minutes. The sections were re-hydrated, washed with phosphate-buffered saline (PBS), and followed by incubation with the ENO1 antiserum (1:2000). The specificity of the antiserum was also examined by staining sections of the same tissue block with pre-immunized serum, antiserum against GST tag, or ENO1 antiserum pre-absorbed with one microgram of membrane-immobilized GST-ENO1 antigen in 1:2000 dilution. After the sections were incubated with biotinylated secondary antibody, the ABC complex was visualized by exposing sections to 3, 3-diaminobenzidine solution (Dako, Carpinteria Calif.) and the slides were counter-stained with hematoxylin.

Results from the IHC experiments are shown in FIG. 6. ENO1 was expressed in 76 out of the 80 samples. Shown are transverse serial sections from a patient with lung adenocarcinoma (Adeno Calif.) and stained with ENO1 antiserum (A) or ENO1 antiserum preabsorbed with immobilized CST-fused ENO1 antigen (B) to show the specificity of ENO1 antiserum. Panel C shows normal-like alveolar epithelial cells proximal to the tumor part (arrows) displayed increasing staining of ENO1 in either cytoplasm, nuclear, or membrane (inset, arrows), whereas the distal alveolar walls showed low basal expression. D, inset, adenocarcinoma cells in another patient also showed high level of cytoplasm staining of ENO1. Magnifications, X100 (A-D) and X200 (C and D, insets). Bar, 100 μm.

Example 7

High ENO1 Expression Correlates with High Invasion Capacity of Human Lung Cancer Cells A weakly invasive human lung cancer cell line, CL1-0, was originally screened in vitro for invasion capacity using a Transwell assay (46). The highly invasive sub-line CL1-5 was obtained through five rounds of selection with the Transwell assay as descried previously (46). The CL1-5 cell line was further selected for in vivo lung metastasis capacity, and a sub-sub-line, CL1-5F4, was obtained after four rounds of in vivo selection (46).

Western blotting was used to assess ENO1 expression on CL1-0 cells, CL1-5 cells, and CL1-5F4 cells. Cell lysates were homogenized and centrifuged at 5,000 rpm for 10 minutes for Western blotting. Thirty micrograms of total lysates from each cell line were separated with 10% SDS-PAGE and transferred to a nitrocellulose membrane. Proteins were detected with rabbit ENO1-specific antiserum (1:5000), obtained as described above, for one hour. β-actin was used as an internal control.

Results from these experiments are shown in FIG. 7A. The increasing density of the band detected via blotting with ENO1-specific antibodies demonstrates that ENO1 expression increased throughout the selection process.

Invasion capacity of each cell line into micropore filters (Becton Dickinson, Franklin Lakes, N.J.) coated with extracellular matrix (matrigel) (Becton Dickinson) was assessed using a Transwell assay. $2\times10^4$ cells were seeded in the top chamber of a two-chamber assay system and incubated for 24 hours with media containing 10% FBS in the lower chamber. The two chambers are separated by a micropore filter (8 μm pore size) coated with matrigel. After the incubation period, the matrigel-coated filters were stained and the number of cells invading into the matrigel-coated filter was quantified under a microscope Results from these experiments are shown in FIG. 7B. These results demonstrate that invasion capacity increased after the selection procedure.

Taking together the results from FIGS. 7A and 7B, the selection procedure resulted in increased ENO1 expression and increased invasion capacity. Consistently, cells expressing a higher level of ENO1 also had a higher invasion capacity. Thus, increased ENO1 expression correlated with increased invasion.

Example 8

Low ENO1 Expression Correlates with Low Invasion Capacity of Human Lung Cancer Cells To determine whether decreased ENO1 expression led to decreased invasion, ENO1 gene expression was down-regulated, using RNA interference, or physically blocked, using ENO1-specific antibodies.

RNA Interference

Stable clones were generated by transfecting CL1-5F4 cells with two micrograms of empty vector or shRNA against ENO1 (5'-AGCTGTTGAGCACATCAATAAA-3') (SEQ ID NO: 7) (Open Biosystems). Cells were then selected using 2 μg/ml puromycin 24 hours post-transfection. One cloned cell line (named vector control, VC) was selected from CL1-5F4 cells transfected with the empty vector. Three cloned cell lines (named C4, C5 and C8) were selected from CL1-5F4 cells transfected with the shRNA against ENO1.

Results demonstrating the reduction of ENO1 expression via Western blot are shown in FIG. 8. Thirty micrograms of protein lysate from CL1-5F4 cells transfected with an empty vector (vector control cells, VC) or with shRNA against ENO1 (C4, C5 and C8 cells) were separated on 10% SDS-PAGE and transferred to a nitrocellulose membrane. Proteins were detected using ENO1-specific antibodies. β-actin was used as internal control of protein loading. Three stable cell lines (C4, C5 and C8) expressed low levels of ENO1 protein compared to cell lines that were not transfected with shRNA constructs.

The migration capacity of CL1-0, CL1-5, and three transfectants was analyzed by an in vitro Transwell assay, without coating the filters with Matrigel, while invasion capacity was determined by the in vitro Transwell assay as described above. Migration capacity was measured by placing $5 \times 10^4$ cells in the top chamber of a two-chamber assay system and incubated for six hours with media containing 10% FBS in the lower chamber. The two chambers are separated by a micropore filter (8 μm pore size). Cells migrating to the opposite side of the filter was stained and counted under a microscope. Invasion capacity was measured by seeding $2 \times 10^4$ cells on the matrigel-coated filter and harvesting invading cells 24 hours later, as described above in Example 7. After the incubation period, the filters were stained and the cell number was quantified by microscopy.

Results from these experiments are shown in FIGS. 9A and 9B. CL1-0 cells were used as a control to exemplify cells with low migration and invasion capacities. These results show that approximately 146.5±31.8 CL1-5F4 cells migrated and 101.5±14.9 CL1-5F4 cells invaded. Transfecting CL1-5F4 with empty vector (vector control cells, VC) had similar results on migration and invasion compared to untransfected CL1-5F4 cells. Transfection with shRNA against ENO1 (C4 and C5 cells) decreased the migration and invasion capacities compared to cells that were transfected with empty vector (vector control cells). These results demonstrate that down-regulation of ENO1 expression can reduce CL1-5F4 cells' migration and invasion capacities.

In vivo Experiments with Human Lung Cancer Cells

To investigate the effect of down-regulating ENO1 in CL1-5 cells on tumor growth and metastasis in vivo, CL1-5F4 cells were first transfected with an empty vector to generate the vector control cell line or with shRNA against ENO1 to generate the C4 and C8 cell lines as described above.

To determine ENO1's effect on tumor growth, $1 \times 10^6$ stable cell clones were then subcutaneously injected into five NOD/SCID mice. Tumor volume was measured every two to three days. The size of tumor was determined as follows: short diameter$^2$×long diameter×½. Each group contains five mice.

Results from these experiments are shown in FIG. 10. CL1-5F4, vector control cells, and C4 cells grew similarly; however, C8 cells grew slightly slower than the other cells tested. These results demonstrate that decreased ENO1 expression has only a minor effect on tumor growth when injected subcutaneously into NOD/SCID mice.

To determine ENO1's effect on metastasis, $2 \times 10^6$ stable clones were intravenously injected through the tail vein into NOD/SCID mice. The number of lung tumor nodules was determined after 28 days.

Results from these experiments are shown in FIG. 11. There were 85±35 pulmonary metastases in CL1-5F4 cells transfected with empty vector (vector control cells) compared to 31±15 and 26±10 pulmonary metastases in cells transfected with shRNA against ENO1 (C4 and C8 cells, respectively). These results indicate that decreased ENO1 expression appears to significantly reduce lung metastasis.

In vivo Experiments with Murine Cancer Cells

B16F1 murine melanoma cells form metastatic lung nodules upon intravenous tail vein injection into C57BL/6 mice. B16F1-L5 cells were established after five rounds of in vivo selection. To select for highly metastatic tumor cells, B16F1 cells were injected into tail vein of a C57BL/6 mice to allow the formation of metastatic tumor nodules in the lung. The tumor nodules were excised and homogenized to produce single cell suspension. The resulting tumor cells (named B16F1-L1) were then cultured in vitro. B16F1-L1 tumor cells were then collected and injected into tail vein of another C57BL/6 mice. Such in vivo selection of highly metastatic tumor cells were repeated four times to generate the B16F1-L5 cell line.

Results demonstrating that intravenous injection of B16F1-L5 into C57BL/6 mice (n=8) generates more tumor nodules compared to the parental B16F1 cell line (p<0.05) are shown in FIG. 12A. There were 172±48 pulmonary metastases in B16F1-L5 cells compared to 52±24 pulmonary metastases in B16F1 parental cells. Additionally, Western blotting with an antibody against murine ENO1 showed that B16F1 cells expressed 75% of the level of ENO1 expressed by the B16F1-L5 cells as seen in FIG. 12B. Blotting with anti-α-tubulin antibodies provided an internal loading control to normalize the expression of mENO1.

Stable clones with decreased ENO1 expression were obtained by transfecting B16F1-L5 cells with an empty vector (vector control cells) or with shRNA against ENO1 (1G9 and 2E11 cells) (5'-ATGTAGACACCGAAGTGAT-3') (SEQ ID NO: 8) (Open Biosystems). To determine whether lower ENO1 levels correlated with reduced metastasis, $2 \times 10^5$ clones were intravenously injected into the tail veins of C57BL/6 mice, and the number of lung tumor nodules was determined 14 days post injection. Each group contained between six and seven mice.

Results from these experiments are shown in FIG. 13A. Similar to the human lung cancer cell line, down regulation of ENO1 expression reduced the number of lung metastasis nodules (P<0.005). There were 235±109 pulmonary metastases in B16F1-L5 cells transfected with the empty vector (vector control cells) compared to 36±24 and 24±27 pulmonary metastases in cells transfected with shRNA against mENO1 (1G9 and 2E11 cells, respectively). Additionally, Western blotting with an antibody against murine ENO1 showed that 1G9 and 2E11 cells expressed 90% and 85%, respectively, of the level of ENO1 expressed by the vector control cells, as seen in FIG. 13B. Blotting with anti-α-tubulin antibodies provided an internal loading control to normalize the expression of mENO1.

Antibody Blockade

CL1-5F4 cells were mixed with ENO1-specific antibodies or control anti-GST antibodies to determine the effect of blocking ENO1 on cell invasion. $2 \times 10^4$ cells were incubated with or without antibodies at 37° C. for 30 minutes and seeded into the upper wells of a Transwell assay as described above.

Results from these experiments are shown in FIG. 14. Cells incubated with ENO1-specific antibodies decreased invasion in a dose-dependent fashion. Thus, incubation with ENO1-specific antibody significantly inhibits the invasion capacity of CL1-5F4 cells.

Example 9

Upregulation of ENO1 and Clinical Outcome

Quantification of ENO1 Expression and Statistical Analysis

To analyze the relationship between the up-regulation of ENO1 and clinical outcome in patients, several different statistical analyses were performed. Eighty patients with NSCLC were included and followed up for 60 months post-surgery. The median follow-up duration of all patients was 29.5 months.

The staining of ENO1 in effusion cells was assessed using the Quick score method (33) at a final magnification of ×200. Samples were independently examined and blindly assessed by two pathologists. Conflicting scores were resolved at a discussion microscope. Both normal lung and tumor control slides (BioGenex, San Ramon, Calif.) were also included in this study. The Quick score method accounted for the intensity and distribution of ENO1 immunoreactivity within tumors. Intensity scores of 0, 1, 2, and 3 stand for negative, weak, moderate, and strong stain, respectively. The proportion of tumor cells showing positive staining was scored as follows: 0%=0, 1-25%=1, 26-50%=2, 51-75%=3, and 76-100%=4. Scores obtained from intensity and distributions of positive staining were added to give a final Quick score that ranged from 0 to 7. The numbers of patients with respect to the intensity and distribution of ENO1 staining are shown in Table 1. For the survival analysis, progression-free survival (PFS) was calculated as survival from the date of surgery to the date of disease recurrence or death. Data for patients who were alive and relapse-free were censored as of the date of the last following-up visit. Overall survival (OS) was calculated as survival from the date of surgery to the date of death. The associations between ENO1 expression status (score < or $\geq$5) and clinical variables were calculated with univariate (Fisher's exact test) and multivariate (Logistic regression) methods. Survival curves for PFS and OS were plotted according to Kaplan-Meier method and significances of differences between groups were analyzed by a log-rank test.

Relationship Between ENO1 Expression and Cancer Development

Results from the above experiments are shown in Table 2 and FIG. 15. Among the 80 patients, 30 patients died from lung cancer and had a median CSS of 10 months ranging from two to 42 months. Forty-five patients experienced disease relapse. Semi-quantification of ENO1 expression status (< or $\geq$5) using Quick score method (34) demonstrated that no statistical differences in age, gender, smoking status, or histological subtypes were found. In contrast, tumor stages and recurrence were tightly associated with expression level of ENO1. Tumors in patients with stage III (93%) or recurrence (89%) had significantly higher ENO1 expression (Score$\leq$5), compared to that in patients with stage I/II (71%) or no detected recurrence (66%) (P=0.018 and P=0.012, respectively).

Survival analysis according to Kaplan-Meier method revealed significant correlation between ENO1 expression status and either PFS or OS in all patients (FIGS. 15A and 15B). Patients with tumors expressing higher levels of ENO1 (Score $\geq$5) tightly correlated with poorer PFS and OS significantly (P=0.0035 and P=0.0027, respectively).

Moreover, to avoid a bias favoring higher ENO1 expression as a poor prognosis marker due to a large number of Stage III tumors with the score higher than 5, only patients with stage I/II disease were selected for further analysis. Results in FIGS. 15C and 15D consistently demonstrated that ENO1 expression level was reversely correlated with PFS and OS significantly (P=0.0015 and P=0.064, respectively). Thus, these data strongly support a potential prognostic role of ENO1 expression for NSCLC patients, even with early Stage I/II diseases.

Cox multivariate analysis was used to test contribution of ENO1 expression status, tumor stage and/or disease recurrence, age, gender, smoking status, histological subtypes on PFS and OS of the patients. Only ENO1 expression with score $\geq$5 proved to be associated with poor PFS (P=0.031). In contrast, stage I/II disease was shown to have a better trend on PFS (P=0.076). Additionally, both lower ENO1 expression (score <5) as well as free of disease recurrence were emerged as strong factors contributing on better OS outcomes (P=0.008 and P=0.003, respectively). Taken together, these data strongly support expression status of ENO1 to be a potent prognostic marker for survival outcomes of NSCLC patients.

Example 10

Low-Level of ENO1 Antibody in Serum of Non-Small Cell Lung Cancer Patient

The levels of serum ENO1 autoantibodies in normal people, in patients with non-cancer associated diseases and in patients with non-small cell lung cancer were specifically measured by a sandwich ELISA assay. Purified GST-ENO1 recombinant protein (0.2 μg/well) was immobilized using GST antibody coated on each well of ELISA plates. ENO1-specific IgG was used as a control antibody to establish a standard curve. Sera were obtained from 5 normal people, 21 patients with non-cancer associated diseases, and 35 patients with non-small cell lung cancer, including adenocarcinoma, squamous cell carcinoma, and large cell carcinoma. The presence of ENO1 autoantibodies in the diluted serum samples (1:10 dilution) of these patients was detected by goat-anti-human IgG conjugated with HRP, visualized by the addition of HRP substrates, ABTS, and read at $OD_{405}$.

Results from these experiments are shown in FIG. 16. The level of the ENO1 autoantibodies in non-small cell lung cancer patients was statistically significantly lower than that of the healthy donors and patients with non-cancer associated diseases (P<0.01).

Example 11

Induction of Anti-ENO1 Humoral Immunity Suppresses Tumor Growth

A vaccination/protection model and a therapy model using the ML1 mouse hepatoma cell line, which expresses ENO1 on the cell surface, was used to evaluate the potential of using ENO1 as the target of vaccine- or antibody-based immunotherapy.

In the vaccination/protection model, Balb/C mice were immunized with 20 μg recombinant mouse ENO1 (mENO1 immunized, n=6), 20 μg GST alone (GST immunized, n=5), or no antigen (control, n=6) at days -30,-15 and -7. The gene encoding mouse ENO1 was cloned out from ML-1 hepatoma cells by RT-PCR with forward primer: 5'-AATTCTA-GACTCTATTCTCAGGATCCA-3' (SEQ ID NO: 9) and backward primer 5'-AATAAGCTTTTATTTGGC-CAGGGGGTT-3' (SEQ ID NO: 10). The amplified gene fragment was double digested with Xba I and Hind III, cloned into pGEX-KG vector, and expressed in *E. coil* cells to generate a GST-tagged recombinant mouse ENO1 protein. Protein purification was performed using glutathione-immobilized affinity chromatography as recommended by the manufacturer (Sigma, St. Louis). The GST protein was purified from *E. coli* cells transfected with the pGEX-KG vector, as described above. All of the mice were then challenged with $1 \times 10^6$ ML1 cells at day zero. Tumor growth was monitored weekly, and animals were bled to detect the presence of ENO1-specific antibodies.

Results from the vaccination/protection model are shown in FIG. 17. ENO1-specific antibodies were present in all mice vaccinated with the recombinant ENO1 (data not shown). Tumor growth was significantly delayed in mice that were vaccinated with GST-mENO1.

In the therapy model, $1 \times 10^6$ ML-1 hepatoma cells were subcutaneously inoculated into each Balb/C mice at day zero. At day 14, the mice were primed with 50 μg of CpG 1826-containing 20 μg of mouse-homologue ENO1 (mENO1) antigen. Control mice were primed with 50 μg of CpG 1826 without the antigen. At days 28 and 35 the mice were boosted with the priming mixture. Tumor size was measured at days 14, 21, 28, 35, and 42. Western blots were performed at day 42 to detect the presence of anti-mENO antibodies in the sera of all mice.

Results from these experiments are shown in FIGS. 18 and 19.

FIG. 18 shows Western blots from the mice 42 days after transfer of the ML-1 hepatoma cells. The left panels show Western blots from individual mice immunized with mENO1 while the rights panels show Western blots from individual control mice. These experiments show that half of the mice that received mENO1 and adjuvant developed antibodies specific to mENO1 (lanes 1-3, left panel) (1:3000 dilution of sera, detected 1 μg/lane of mENO1 in 10 seconds) while half of the mice that received mENO1 and adjuvant did not produce detectable anti-mENO antibodies (lanes 4-6, left panel). Control mice did not produce detectable anti-mENO1 antibodies (lanes 1-6, right panel). Equal loading of mENO1 in each lane of the Western blots described above was verified by running separate Western blots and detecting with a control anti-mENO1 antibody (bottom panels).

FIG. 19 shows tumor sizes from the mice that generated detectable anti-mENO1 antibodies (anti-mENO1 Ab (+), ♦), mice that did not produce detectable anti-mENO1 antibodies (anti-mENO Ab (-), ■), and control mice (▲). Forty-two days after ML-1 hepatoma cell-transfer, tumor sizes were smaller in mice that generated detectable anti-mENO1 antibodies compared to mice that did not produce detectable mENO1 antibodies and control mice. These results indicate that development of a strong anti-ENO antibody response may reduce tumor size.

REFERENCES

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

1. Andrews, B. S., Arora, N. S., Shadforth, M. F., Goldberg, S. K., and Davis, J. S. t. 1981. The role of immune complexes in the pathogenesis of pleural effusions. Am Rev Respir Dis 124:115-120.
2. Zeng, C. Q., Alpert, L. C., and Alpert, E. 1992. Characterization of a lung cancer-associated auto-antigen. Int J Cancer 52: 523-529.
3. Gorsky, Y., Weiss, I., and Sulitzeanu, D. 1977. Complexes of breast-cancer-associated antigen(s) and corresponding antibodies in pleural effusions from a patients [sic] with breast cancer. Isr J Med Sci 13:844-847.
4. Lai, C. L., Tsai, C. M., Tsai, T. T., Kuo, B. I., Chang, K. T., Fu, H. T., Perng, R. P., and Chen, J. Y. 1998. Presence of serum anti-p53 antibodies is associated with pleural effusion and poor prognosis in lung cancer patients. Clin Cancer Res 4:3025-3030.
5. Wang, D. Y., Yang, P. C., Yu, W. L., Kuo, S. H., and Hsu, N. Y. 2000. Serial antinuclear antibodies titer in pleural and pericardial fluid. Eur Respir J 15:1106-1110.
6. Yamamoto, A., Shimizu, E., Sumitomo, K., Shinohara, A., Namikawa, O., Uehara, H., and Sone, S. 1997. L-Myc overexpression and detection of auto-antibodies against L-Myc in both the serum and pleural effusion from a patient with non-small cell lung cancer. Intern Med 36:724-727.
7. Miedouge, M., Rouzaud, P., Salama, G., Pujazon, M. C., Vincent, C., Mauduyt, M. A., Reyre, J., Carles, P., and Serre, G. 1999. Evaluation of seven tumour markers in pleural fluid for the diagnosis of malignant effusions. Br J Cancer 81:1059-1065.
8. Amirghofran, Z., Sheikhi, A. K., Kumar, P. V., and Saberi Firouzi, M. 2002. Soluble HLA class I molecules in malignant pleural and peritoneal effusions and its possible role on NK and LAK cytotoxicity. J Cancer Res Clin Oncol 128:443-448. Epub 2002 August 2009.
9. Kim, J. W., and Dang, C. V. 2005. Multifaceted roles of glycolytic enzymes. Trends Biochem Sci 30:142-150.
10. Pancholi, V. 2001. Multifunctional alpha-enolase: its role in diseases. Cell Mol Life Sci 58:902-920.
11. Redlitz, A., Fowler, B. J., Plow, E. F., and Miles, L. A. 1995. The role of an enolase-related molecule in plasminogen binding to cells. Eur J Biochem 227:407-415.
12. Jiang, B. H., Agani, F., Passaniti, A., and Semenza, G. L. 1997. V-SRC induces expression of hypoxia-inducible factor 1 (HIF-1) and transcription of genes encoding vascular endothelial growth factor and enolase 1: involvement of HIF-1 in tumor progression. Cancer Res 57:5328-5335.
13. Ray, R. B., and Steele, R. 1997. Separate domains of MBP-1 involved in c-myc promoter binding and growth suppressive activity. Gene 186:175-180.

14. Gitlits, V. M., Toh, B. H., and Sentry, J. W. 2001. Disease association, origin, and clinical relevance of autoantibodies to the glycolytic enzyme enolase. J Investig Med 49:138-145.
15. Gomm, S. A., Keevil, B. G., Thatcher, N., Hasleton, P. S., and Swindell, R. S. 1988. The value of tumour markers in lung cancer. Br J Cancer 58:797-804.
16. Miyazaki, A., Sato, N., Takahashi, S., Sasaki, A., Kohama, G., Yamaguchi, A., Yagihashi, A., and Kikuchi, K. 1997. Cytotoxicity of histocompatibility leukocyte antigen-DR8-restricted CD4 killer T cells against human autologous squamous cell carcinoma. Jpn J Cancer Res 88:191-197.
17. Sato, N., Nabeta, Y., Kondo, H., Sahara, H., Hirohashi, Y., Kashiwagi, K., Kanaseki, T., Sato, Y., Rong, S., Hirai, I., et al. 2000. Human CD8 and CD4 T cell epitopes of epithelial cancer antigens. Cancer Chemother Pharmacol 46:S86-90.
18. Chen, Y. T. 2000. Cancer vaccine: identification of human tumor antigens by SEREX. Cancer J 6:S208-217.
19. Peebles, K. A., Duncan, M. W., Ruch, R. J., and Malkinson, A. M. 2003. Proteomic analysis of a neoplastic mouse lung epithelial cell line whose tumorigenicity has been abrogated by transfection with the gap junction structural gene for connexin 43, Gja1. Carcinogenesis 24:651-657.
20. Zhang, L., Cilley, R. E., and Chinoy, M. R. 2000. Suppression subtractive hybridization to identify gene expressions in variant and classic small cell lung cancer cell lines. J Surg Res 93:108-119.
21. Wu, W., Tang, X., Hu, W., Lotan, R., Hong, W. K., and Mao, L. 2002. Identification and validation of metastasis-associated proteins in head and neck cancer cell lines by two-dimensional electrophoresis and mass spectrometry. Clin Exp Metastasis. 19:319-326.
22. Hennipman, A., Smits, J., van Oirschot, B., van Houwelingen, J. C., Rijksen, G., Neyt, J. P., Van Unnik, J. A., and Staal, G. E. Glycolytic enzymes in breast cancer, benign breast disease and normal breast tissue.251-263.
23. Altenberg, B., and Greulich, K. O. 2004. Genes of glycolysis are ubiquitously overexpressed in 24 cancer classes. Genomics 84:1014-1020.
24. Chang, Y. S., Wu, W., Walsh, G., Hong, W. K., and Mao, L. 2003. Enolase-alpha is frequently down-regulated in non-small cell lung cancer and predicts aggressive biological behavior. Clin Cancer Res 9:3641-3644.
25. Gatenby, R. A., and Gillies, R. J. 2004. Why do cancers have high aerobic glycolysis? Nat Rev Cancer 4:891-899.
26. Chen, Y. M., Tsai, C. M., Whang-Peng, J., and Perng, R. P. 2002. Double signal stimulation was required for full recovery of the autologous tumor-killing effect of effusion-associated lymphocytes. Chest 122:1421-1427.
27. Masuda, N., Fukuoka, M., Takada, M., Kudoh, S., and Kusunoki, Y. 1991. Establishment and characterization of 20 human non-small cell lung cancer cell lines in a serum-free defined medium (ACL-4). Chest 100:429-438.
28. Ueyama, H., Sasaki, I., Shimomura, K., and Suganuma, M. 1995. Specific protein interacting with a tumor promoter, debromoaplysiatoxin, in bovine serum is alpha 1-acid glycoprotein. J Cancer Res Clin Oncol. 121:211-218.
29. Nesterenko, M. V., Tilley, M., and Upton, S. J. 1994. A simple modification of Blum's silver stain method allows for 30 minute detection of proteins in polyacrylamide gels. J Biochem Biophys Methods 28:239-242.
30. Gharahdaghi, F., Weinberg, C. R., Meagher, D. A., Imai, B. S., and Mische, S. M. 1999. Mass spectrometric identification of proteins from silver-stained polyacrylamide gel: a method for the removal of silver ions to enhance sensitivity. Electrophoresis 20:601-605.
31. Perkins, D. N., Pappin, D. J., Creasy, D. M., and Cottrell, J. S. 1999. Probability-based protein identification by searching sequence databases using mass spectrometry data. Electrophoresis 20:3551-3567.
32. Shih, N. Y., Li, J., Karpitskii, V., Nguyen, A., Dustin, M. L., Kanagawa, O., Miner, J. H., and Shaw, A. S. 1999. Congenital nephrotic syndrome in mice lacking CD2-associated protein. Science 286:312-315.
33. Barnes, D. M., Harris, W. H., Smith, P., Millis, R. R., and Rubens, R. D. 1996. Immunohistochemical determination of oestrogen receptor: comparison of different methods of assessment of staining and correlation with clinical outcome of breast cancer patients. Br J Cancer 74:1445-1451.
34. Rhodes, A., Jasani, B., Barnes, D. M., Bobrow, L. G., and Miller, K. D. 2000. Reliability of immunohistochemical demonstration of oestrogen receptors in routine practice: interlaboratory variance in the sensitivity of detection andevaluation of scoring systems. J Clin Pathol 53:125-130.
35. Semenza, G. L., Jiang, B. H., Leung, S. W., Passantino, R., Concordet, J. P., Maire, P., and Giallongo, A. 1996. Hypoxia response elements in the aldolase A, enolase 1, and lactate dehydrogenase A gene promoters contain essential binding sites for hypoxia-inducible factor 1. J Biol Chem 271:32529-32537.
36. Kim, J. W., Zeller, K. I., Wang, Y., Jegga, A. G., Aronow, B. J., O'Donnell, K. A., and Dang, C. V. 2004. Evaluation of myc E-box phylogenetic footprints in glycolytic genes by chromatin immunoprecipitation assays. Mol Cell Biol 24:5923-5936.
37. Holland, J. P., Labieniec, L., Swimmer, C., and Holland, M. J. 1983. Homologous nucleotide sequences at the 5' termini of messenger RNAs synthesized from the yeast enolase and glyceraldehyde-3-phosphate dehydrogenase gene families. The primary structure of a third yeast glyceraldehyde-3-phosphate dehydrogenase gene. J Biol Chem 258:5291-5299.
38. Giallongo, A., Feo, S., Moore, R., Croce, C. M., and Showe, L. C. 1986. Molecular cloning and nucleotide sequence of a full-length cDNA for human alpha-enolase. Proc Natl Acad Sci USA 83:6741-6745.
39. Muller, A. J., Duhadaway, J. B., Donover, P. S., Sutanto-Ward, E., and Prendergast, G. C. 2005. Inhibition of indoleamine 2,3-dioxygenase, an immunoregulatory target of the cancer suppression gene Bin1, potentiates cancer chemotherapy. Nat Med 11:312-319. Epub 2005 February 2013.
40. Dong, H., Strome, S. E., Salomao, D. R., Tamura, H., Hirano, F., Flies, D. B., Roche, P. C., Lu, J., Zhu, G., Tamada, K., et al. 2002. Tumor-associated B7-H1 promotes T-cell apoptosis: a potential mechanism of immune evasion. Nat Med 8:793-800. Epub 2002 June 2024.
41. Nakashima, M., Sonoda, K., and Watanabe, T. 1999. Inhibition of cell growth and induction of apoptotic cell death by the human tumor-associated antigen RCAS1. Nat Med 5:938-942.
42. Dong, H., Strome, S. E., Matteson, E. L., Moder, K. G., Flies, D. B., Zhu, G., Tamura, H., Driscoll, C. L., and Chen, L. 2003. Costimulating aberrant T cell responses by B7-H1 autoantibodies in rheumatoid arthritis. J Clin Invest 111: 363-370.
43. Ray, R., and Miller, D. M. 1991. Cloning and characterization of a human c-myc promoter-binding protein. Mol Cell Biol 11:2154-2161.

44. Ghosh, A. K., Steele, R., and Ray, R. B. 1999. MBP-1 physically associates with histone deacetylase for transcriptional repression. Biochem Biophys Res Commun 260:405-409.
45. Ray, R. B., Steele, R., Seftor, E., and Hendrix, M. 1995. Human breast carcinoma cells transfected with the gene encoding a c-myc promoter-binding protein (MBP-1) inhibits tumors in nude mice. Cancer Res 55:3747-3751.
46. Chu, Y. W., Yang, P. C., Yang, S. C., Shyu, Y. C., Hendrix, M. J., Wu, R., and Wu, C. W. 1997. Selection of invasive and metastatic subpopulations from a human lung adenocarcinoma cell line. Am J Respir Cell Mol Biol 17:353-36
47. Collins, F. S. and Trent, J. M. 2001. Cancer Genetics. Harrison's Principles of Internal Medicine 503.
48. Fenton, R. G. and Longo, D. L. 2001. Cell Biology of Cancer. Harrison's Principles of Internal Medicine 509.
49. Abbas, A. K., Lichtman, A. H., and Pober, J. S. 2000. Cellular and Molecular Immunology 386-391.
50, Light, R. W. 2001. Disorders of the Pleura, Mediastinum, and Diaphragm. Harrison's Principles of Internal Medicine 1513-1514.

TABLE 1

| Distribution | Intensity | | | |
| --- | --- | --- | --- | --- |
| | 0 (negative) | 1 (weak) | 2 (moderate) | 3 (strong) |
| 0 (0%) | 0 | 0 | 0 | 0 |
| 1 (1-25%) | 0 | 0 | 2 | 2 |
| 2 (26-50%) | 0 | 0 | 8 | 16 |
| 3 (51-15%) | 0 | 5 | 14 | 17 |
| 4 (76-100%) | 0 | 5 | 4 | 7 |

TABLE 2

| Variable | ENO1 expression | | | | |
| --- | --- | --- | --- | --- | --- |
| | Total, n (%) | Score < 5, n (%) | Score ≧ 5, n (%) | P (univariate) | P (multlvariate) |
| Quick score | 80 (100) | 17 (21) | 63 (79) | 1.0 | 0.926 |
| Medium age (y) | | | | | |
| <65 | 29 (36) | 6 (21) | 23 (79) | 1.0 | 0.926 |
| ≧65 | 51 (64) | 11 (22) | 40 (78) | | |
| Gender | | | | | |
| Male | 69 (66) | 15 (22) | 54 (76) | 1.0 | 0.789 |
| Female | 11 (14) | 2 (18) | 9 (82) | | |
| Smoking status | | | | | |
| No | 25 (31) | 8 (37) | 17 (68) | 1.0 | 0.665 |
| Yes | 55 (69) | 15 (27) | 40 (73) | | |
| Histology | | | | | |
| SCC | 40 (50) | 8 (20) | 32 (80) | 1.0 | 0.785 |
| Non-SCC | 40 (50) | 9 (22) | 31 (78) | | |
| AdenoCA | 31 (39) | 6 (19) | 25 (81) | 0.787 | 0.742 |
| Non-adenoCA | 49 (61) | 11 (22) | 38 (78) | | |
| Stage | | | | | |
| I + II | 51 (64) | 15 (29) | 36 (71) | 0.022* | 0.018* |
| III | 29 (36) | 2 (7) | 27 (93) | | |
| Recurrence | | | | | |
| No | 35 (44) | 12 (34) | 23 (66) | 0.015* | 0.012* |
| Yes | 45 (56) | 5 (11) | 40 (89) | | |

NOTE:
Univariate analysis was done using Fisher's exact test. Multivariate analysis was done using logistic regression method.
Abbreviations:
SCC, squamous cell carcinoma; adenoCA, adenocarcinoma.
*P < 0.05, indicates statistically significant.

What is claimed is:

1. A method of suppressing tumor growth comprising
   (a) identifying a patient having at least one of lung cancer, colon cancer, breast cancer, or liver cancer, and wherein the patient has a lower level of anti-ENO1 autoantibody compared to patients with non-cancer-associated diseases and healthy subjects;
   (b) administering ENO1 antigen to the patient; and
   (c) determining whether administration of the ENO1 antigen increases the level of anti-ENO1 antibody in the patient; wherein tumor growth is suppressed in patients with increased levels of anti-ENO1 antibody after administration of the ENO1 antigen.

2. The method of claim 1, further comprising measuring the size of the tumor.

3. The method of claim 1, wherein the ENO1 antigen is administered with an adjuvant.

4. The method of claim 1, wherein the cancer is non-small cell lung cancer.

5. The method of claim 4, wherein the non-small cell lung cancer is selected from adenocarcinoma, squamous cell carcinoma, and large cell carcinoma.

* * * * *

SEQUENCE LISTING

```
<160> NUMBER OF SEQ ID NOS: 16

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
```
ggtggaattc tatctattct caagatccat gcc                                    33

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
actccatggt tacttggcca aggggtttct                                        30

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
attgaattct tccatagaga agatctgggc ccgggagat                              39

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
attgaattct cacagcacac tgggattacg gaag                                   34

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agggaattct gccatgcaga aaatctttgc                                        30

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
attgaattct cacttggcct tcgggtt                                           27

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agctgttgag cacatcaata aa                                                22

-continued

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atgtagacac cgaagtgat                                                19

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aattctagac tctattctca ggatcca                                       27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aataagcttt tatttggcca gggggtt                                       27

<210> SEQ ID NO 11
<211> LENGTH: 11
<212> TYPE: PRT
<213> ORGANISM: Homo sapiens

<400> SEQUENCE: 11

Leu Met Ile Glu Met Asp Gly Thr Glu Asn Lys
 1               5                  10

<210> SEQ ID NO 12
<211> LENGTH: 13
<212> TYPE: PRT
<213> ORGANISM: Homo sapiens

<400> SEQUENCE: 12

Gly Asn Pro Thr Val Glu Val Asp Leu Phe Thr Ser Lys
 1               5                  10

<210> SEQ ID NO 13
<211> LENGTH: 12
<212> TYPE: PRT
<213> ORGANISM: Homo sapiens

<400> SEQUENCE: 13

Tyr Ile Ser Pro Asp Gln Leu Ala Asp Leu Tyr Lys
 1               5                  10

<210> SEQ ID NO 14
<211> LENGTH: 15
<212> TYPE: PRT
<213> ORGANISM: Homo sapiens

```
-continued

<400> SEQUENCE: 14

Val Asn Gln Ile Gly Ser Val Thr Glu Ser Leu Gln Ala Cys Lys
1               5                   10                  15

<210> SEQ ID NO 15
<211> LENGTH: 19
<212> TYPE: PRT
<213> ORGANISM: Homo sapiens

<400> SEQUENCE: 15

Asp Ala Thr Asn Val Gly Asp Glu Gly Gly Phe Ala Pro Asn Ile Leu
1               5                   10                  15

Glu Asn Lys

<210> SEQ ID NO 16
<211> LENGTH: 20
<212> TYPE: PRT
<213> ORGANISM: Homo sapiens

<400> SEQUENCE: 16

Phe Thr Ala Ser Ala Gly Ile Gln Val Val Gly Asp Asp Leu Thr Val
1               5                   10                  15

Thr Asn Pro Lys
            20
```